United States Patent [19]
Rochette-Egly et al.

[11] Patent Number: 5,663,303
[45] Date of Patent: Sep. 2, 1997

[54] ANTIBODIES SPECIFIC FOR RETINOIC ACID RECEPTOR-γ

[75] Inventors: Cecille Rochette-Egly; Yves Lutz, both of Strasbourg; Michael Saunders, Ostwald; Isabelle Scheuer, Hagulnau; Marie-Pierre Gaub, Strasbourg; Pierre Chambon, Blaesheim, all of France

[73] Assignees: Institut National de la Santé et de la Recherche Médicale; Centre National de la Recherche Scientifique; Université Louis Pasteur, Strasbourg I, all of Paris, France; E.R. Squibb & Sons, Inc., Princeton, N.J.

[21] Appl. No.: 789,912

[22] Filed: Nov. 4, 1991

[51] Int. Cl.⁶ .................... G01N 33/53; C07K 16/28
[52] U.S. Cl. .................... 530/388.2; 530/387.1; 530/391.3; 530/391.1; 435/7.92; 435/332; 435/334; 436/518
[58] Field of Search .................... 435/7.92, 70.21, 435/240.27; 530/387.1, 388.2, 391.3, 391.1, 389.1; 935/89, 103, 95, 108; 436/547, 518

[56] References Cited

U.S. PATENT DOCUMENTS 4,391,904  7/1983  Litman et al. .................... 435/7

OTHER PUBLICATIONS

Roitt (1991) "Essential Immunology", Blackwell Scientific Publications, Oxford, pp. 65–68 & 74.
Rochette-Egly et al (1991) J. Cell Biol. 115(2):535–545 (Oct. issue).
Harlow et al (1988) "Antibodies: A Laboratory Manual", Cold Spring Harbor Press, New York, pp. 72–77, 92–97, 128–135, 141–157, 321–329 & 519–523.
Beato, *Cell* 56:335–344 (1989).
Benbrook et al., *Nature* 333:669–672 (1988).
Brand et al., *Nature* 332:850–853 (1988).
Brockes, *Neuron* 2:1285–1294 (1989).
Brockes, *Nature* 345:766–768 (1990).
Dollé et al., *Nature* 342:702–705 (1989).
Dollé et al., *Development* 110:1133–1151 (1990).
de Thé et al., *Nature* 343:177–180 (1990).
Eichele, *Trends in Genetics* 5(8):247–251 (1989).
Evans, *Science* 240:889–895 (1988).
Gaub et al., *Proc. Natl. Acad. Sci. USA* 86:3089–3093 (1989).
Giguère et al., *Mol. Cell. Biol.* 10(5):2335–2340 (1990).
Giguère et al., *Nature* 330:624–629 (1987).
Green et al., *Trends in Genetics* 4(11):309–314 (1988).
Kastner et al., *Proc. Natl. Acad. Sci. USA* 87:2700–2704 (1990).
Krust et al., *Proc. Natl. Acad. Sci. USA* 86:5310–5314 (1989).
Krust et al., *EMBO J.* 5(5):891–897 (1986).
LaRosa et al., *Proc. Natl. Acad. Sci. USA* 85:329–333 (1988).
Leroy et al., *EMBO J.* 10(1):59–69 (1991).
Loh et al., *Science* 243:217–220 (1989).
Maden, *Nature* 295:672–675 (1982).
Murphy et al., *Proc. Natl. Acad. Sci. USA* 85:5587–5591 (1988).
Nicholson et al., *EMBO J.* 9(13):4443–4454 (1990).
Okamoto et al., *Cell* 60:461–472 (1990).
Ruberte et al., *Development* 111:45–60 (1991).
Ruberte et al., *Development* 108:213–222 (1990).
Simeone et al., *Nature* 346:763–766 (1990).
Slack, *Nature* 327:553–554 (1987).
Slack, *TIBS* 12:200–204 (1987).
Sucov et al., *Proc. Natl. Acad. Sci. USA* 87:5392–5396 (1990).
Summerbell et al., *TINS* 13(4):142–147 (1990).
Tasset et al., *Cell* 62:1177–1187 (1990).
Thaller et al., *Nature* 327:625–628 (1987).
Tora et al., *EMBO J.* 7(12):3771–3778 (1988).
Tora et al., *Nature* 333:185–188 (1988).
Vasios et al., *Proc. Natl. Acad. Sci. USA* 86:9099–9103 (1989).
Wang et al., *Proc. Natl. Acad. Sci. USA* 80:5880–5884 (1983).
Zelent et al., *Nature* 339:714–717 (1989).
Zelent et al., *EMBO J.* 10(1):71–81 (1991).

*Primary Examiner*—Toni R. Scheiner
*Attorney, Agent, or Firm*—Sterne, Kessler, Goldstein & Fox, P.L.L.C.

[57] ABSTRACT

The present invention discloses methods for preparing antibodies which bind to specific isoforms of the human retinoic acid receptor-γ (RAR-γ). In addition, several monoclonal antibodies are described which bind to human RAR-γ, but not to mouse or which bind to RAR-γ1, but not to RAR-γ2. Methods and kits are described which allow one to detect the isotype of RAR-γ which is expressed in a test sample. Such methods are useful in determining the tissue specific pattern of expression of various RAR-γ isoforms.

10 Claims, 7 Drawing Sheets

Peptide SP15 (A1 region) Ab1γ1 (A1)

mouse  FEHLSPSFRGLG
 human  39----------50

Peptide SP81 (D2 region) Ab5γ (D2)

mouse  KEEGSPDSYELS
 human  172----------183

Peptide SP14 (mouse F region) Ab2γ (mF), RPγ(mF)

mouse  SSEDEAPGGQGKRGQS
 human  -----V------G-LK
      436     451

Peptide SP25 (human F region) Ab4γ (hF)

mouse  K-----K------A
 human  QPGPHPNASSEDEV
      428    441

| Protein kinases | Possible phosphorylation recognition motifs |
|---|---|
| | in the A/B domain |
| cyclic AMP-dependent kinase | 34 R G S* |
| casein kinase I | 40 E M L S* |
| | 57 E M A S* |
| | 64 E T Q S* |
| casein kinase II | 18 S*G Y P |
| | 67 S*T S S |
| | 69 S*S E E |
| proline-dependent kinase | 36 S*P |
| | 43 S*P |
| | 77 S*P |
| | 79 S*P |
| | in the D domain |
| casein kinase I | 173 E E G S* |
| casein kinase II | 176 S*P D S |
| glycogen synthase kinase 3 | 179 S*Y E L S |
| proline-dependent kinase | 176 S*P |
| | 183 S*P |

FIG. 6

ANTIBODIES SPECIFIC FOR RETINOIC ACID RECEPTOR-γ

FIELD OF THE INVENTION

The present invention relates to the generation of antibodies which bind selectively to either mouse or human retinoic acid receptor -gamma, RAR-γ, to hybridomas which produce the above-described antibodies, to a method for preparing hybridomas which produce the above described antibodies, to polypeptides which are used in immunizing animals to produce the antibodies.

DESCRIPTION OF THE RELATED ART

A. Retinoic Acid Receptor γ

Retinoic acid (RA) is a vitamin A metabolite which has been found to be a natural morphogen (Maden et al. Nature 295:672–675 (1982); Tickle et al., Nature 296:564–566 (1982); Slack, J. M. W., Nature 327:553–554 (1987a), Slack, J. M. W., Trends Biochem. Sci. 12:200–204 (1987b); Thaller et al., Nature 327:625–628 (1987)). As a morphogen, RA plays a crucial role in the development and homeostasis of vertebrates (for reviews see Maden, M., Trends Genet. 1:103–104 (1985); Brockes, J. P., Neuron 2:1285–1294 (1989); Brockes, J. P., Nature 345:766–768 (1990); Eichele, G., Trends Genet. 5:246–251 (1989); Summerbell et al., Trends Neurosci. 13:142–147 (1990); and references therein). RA exerts a broad spectrum of effects on various cells in culture and during embryonic and early development of an organism. During development RA effects changes in the expression patterns of specific genes (Wang et al., Proc. Natl. Acad. Sci. USA 80:5880–5884 (1983); LaRosa et al., Proc. Natl. Acad. Sci. USA 85:329–333 (1988); Murphy et al., Proc. Natl. Acad. Sci. USA 85:5587–5591 (1988); Vasios et al., Proc. Natl. Acad. Sci. USA 86:9099–9103 (1989); Okamoto et al., Cell 60:461–472 (1990); Simeone et al., Nature 346:763–766 (1990)), indicating that RA may directly affect gene expression (Zelent et al., EMBO J. 10:71–81 (1991)).

Recently, three highly related nuclear retinoic acid receptors (RAR-α, -β and -γ) have been identified in both human and mouse (Giguère et al., Nature 330:624–629 (1987); Petkovich et al., Nature 330:444–450 (1987); Benbrook et al., Nature 333:669–672 (1988); Brand et at, Nature 332:850–853 (1988); Krust et al., Proc. Natl. Acad. Sci. USA 86:5310–5314 (1989); Zelent et al., Nature 339:714–717 (1989)). These receptors have been shown to belong to the superfamily of steroid/thyroid hormone nuclear receptors which act as ligand-inducible transcriptional enhancer factors ((for review see Evans, R. M., Science 240:889–895 (1988); Green et al., Trends Genet. 4:309–314 (1988); Beato, M., Cell 56:335–344 (1989)).

Similarly to the other members of the nuclear receptor superfamily, RARs have a modular structure which is comprised of six regions designated A to F (Krust et al., EMBO J., 5:891–897 (1986); Green et al., Trends Genet., 4:309–314 (1988)). In this family of steroid receptors, it has been shown that regions C and E are responsible for DNA and ligand binding (Evans, R. M., Science 240:889–895 (1988); Green et al., T.I.G. 4:309–314 (1988)), respectively, and that the A/B and E regions contain distinct trans-activation domains which are both cell type- and promoter-specific (Tora et al., Nature 333:185–188 (1988a); Toro et al., EMBO J., 7:3371–3778 (1988b); Tasset et al., Cell 62:1177–1187 (1990)). The precise roles of regions D and F are unknown.

Recently, multiple human and mouse RAR-γ cDNA isoforms have been characterized (Krust et al., Proc. Natl. Acad. Sci. USA 86:5310–5314 (1989); Giguère et al., Mol. Cell. Biol. 10:2335–2340 (1990); Kastner et al., Proc. Natl. Acad. Sci. USA 87:2700–2704 (1990)). Using anchored PCR (Loh et al., Science 243:217–220 (1989)) and cDNA library screening procedures, a total of six novel mRAR-γ cDNA isoforms (mRAR-γ2 to γ7) have been isolated (Kastner et al., Proc. Natl. Acad. Sci. USA 87:2700–2704 (1990)).

Together with the initially characterized mouse and human RAR-γ1 isoform (formerly termed RAR-γ0, Giguère et al., Nature 330:624–629 (1987); Krust et al., Proc. Natl. Acad. Sci. USA 86:5310–5314 (1989); Zelent et al, Nature 339:714–717 (1989)), the 7 RAR-γ isoforms share a common B-F region. However, their sequences diverge upstream of the A/B region junction (Kastner et al., Proc. Natl. Acad. Sci. USA 87:2700–2704 (1990)).

Human and mouse RAR-α, β and γ share extensive amino acid identity in the two regions that correspond to the DNA binding (region C) and the retinoic acid binding (region E) domains. However, in any given species these receptors are very different in their amino (region A/B) and carboxyl (region F) terminal regions. (Krust et al. Proc. Natl. Acad. Sci. USA 86:5310–5314 (1989); Zelent et al. Nature 339:714–717 (1981). These observations suggest that the three RARs may be functionally distinct, and thus may regulate the expression of different sets of RA-responsive genes.

This view is further supported by the analysis of the distribution of RAR transcripts using Northern blotting (Krust et al., Proc. Natl. Acad. Sci. USA 86:5310–5314 (1989); Zelent et al., Nature 339:714–717 (1989)) and in situ hybridization (Dollè et al., Nature 342:702–705 (1989); Dollè et al., Develop. 110:1133–1151 (1990); Ruberte et al., Develop. 108:213–222 (1990); Ruberte et al., Develop. 111:45–60 (1991)), which showed that each mouse RAR (mRAR) subtype exhibits a specific pattern of expression either in adult tissues or in a developing embryo. Specifically, the localization of RAR-γ transcripts during embryogenesis as determined by in situ hybridization, suggests that RAR-γ plays an important role during early morphogenesis and differentiation of cartilage and cornified squamous epithelia (Dollè et al., Nature 342:702–705 (1989); Dollè et al., Develop. 110:1133–1151 (1990); Ruberte et al., Develop. 108:213–222 (1990); Ruberte et al., Develop. 111:45–60 (1991)).

The two most abundant isoforms of RAR-γ found in mouse, mRAR-γ1 and mRAR-γ2, differ in both their 5'-untranslated region (5'-UTR) and A region sequences. These isoforms were found to be differentially expressed in adult tissues and during the course of embryogenesis, as determined by Northern blot analysis ((Leroy et al. EMBO J. 10:59–69 (1991); (Kastner et al., Proc. Natl. Acad. Sci. USA 87:2700–2704 (1990)).

Recently, polyclonal rabbit antibodies directed against synthetic peptides specific to either RAR-α or RAR-β have been generated (Gaub et al. Proc. Natl. Acad. Sci. USA 86:3089–3093 (1989)). These antibodies were used to detect and localize the expression of RAR α or β in RA-responsive promyelocytic leukemia cell lines.

Until now, it has not been possible to localize the RAR-γ protein in tissues. In order to understand the role of RA in the development and homeostasis of vertebrates it is necessary to specifically identify the cell types which express the specific RA receptors in response to stimuli.

The present invention provides antibodies capable of recognizing RAR-γ or specific isoforms of RAR-γ. Such antibodies will be of important use in understanding the processes and mechanisms of development.

RAR Expression in Skin Tissues

Skin has been found to be the major target organ for RA, both in normal and pathological states (Fuch E. Trends Genet. 4:277–281 (1988) Dhouailly, D. et al., L Embryol. Exp. Morph. 58:63–78 (1980). Additionally, retinoic acid has been demonstrated to have effects on the differentiation and maintenance of epithelial cells in vivo and in vitro (Lotan, R. Biochem. Biophys. Act, 605:33–91 (1980); Roberts et al. in The Retinoids Vol. 2, p.209–286 Academic Press Orlando (1984)).

Retinoids have been used in the treatment of actinally aged skin (Ellis et al., Pharmacol. Skin. 3:249–253 (1989)), various types of dermatoses (Gollnick, Dermatologica 175 (1):182–195 (1987)), disorders of keratinization (Happle et al., Dermatologica 175(1):107–124 (1987)), rheumatoid arthritis (Brinckerhoff et al., 1985 Retinoids, Differentiation and Disease, Pitman, London (Ciba Foundation Symposium 113) p. 191–211), basal cell carcinoma (Peck, Dermatologica 175(1):138–144 (1987)), and systemic sclerosis (Maurice et al., Pharmacol. Skin. 3:235–239 (1989)). In addition, retinoids have been demonstrated to possess immunostimulating activity (Dennell, 1985 Retinoids, Differentiation and Disease, Pitman, London (Ciba Foundation. Symposium 113) p. 117–131), inhibit epidermal terminal differentiation (Lichti et al., 1985 Retinoids, Differentiation and Disease, Pitman, London (Ciba Foundation Symposium 113) p. 77–89), modulate carcinogenesis in the urinary bladder (Hicks et al., 1985 Retinoids, Differentiation and Disease, Pitman, London (Ciba Foundation Symposium 113) p.168–190), regulate differentiation in embryonal carcinoma cells (Sherman et al., 1985 Retinoids, Differentiation and Disease, Pitman, London (Ciba Foundation Symposium 113) p. 42–60), regulate differentiation in tracheal epithelial cells (Jetten et al., 1985 Retinoids, Differentiation and Disease, Pitman, London (Ciba Foundation Symposium 113) p. 61–76), inhibit neoplastic transformation (Bertram et al., 1985 Retinoids, Differentiation and Disease, Pitman, London (Ciba Foundation Symposium 113) p. 29–41), possess anti-inflammatory activity (Ney et al., Dermatologica 175(1):93–99 (1987)), and modulate melanoma growth (Amos et al., Pharmacol. Skin. 3:29–36 (1989)).

It is unknown what the molecular basis is for the various effects retinoids are able to stimulate. One possibility is that the various effects stimulated by retinoids are caused by the interactions of retinoids with the various RAR receptors or with RAR receptors on various tissues. Using the antibodies of the present invention it is now possible to examine the interactions of retinoids with each of the classes of receptors. Such study will lead to a better understanding of the biological effects stimulated by retinoids. For example, since retinoids have been used as an effective treatment Of several skin disorders (Peck GL, The Retinoids Roberts et al., Academic Press, Orlando, p. 391–411 (1984); Kopen et al., J. Cell. Biol., 105:427–440 (1987)); Brown et al. Differentiation 28:268–278 (1985), and RAR-γ is the only retinoic acid receptor thus far identified whose expression is restricted to skin tissues (Zelent et al., Nature, 339:714–717 (1989)), the understanding of the tissue specific expression patterns of various RA receptors will provide the basis of future therapies for skin disorders such as psoriasis, skin cancer, myeloma and other pigmented skin lesions.

SUMMARY OF THE INVENTION

The present invention is based on the generation of monoclonal and polyclonal antibodies which bind selectively to 1) either mouse or human RAR-γ but not to both, 2) RAR-γ1 but not to RAR-γ2, 3) the F region of both human and mouse RAR-γ, and 4) the D2 region of both human and mouse RAR-γ.

The invention additionally provides diagnostic and therapeutic usage for all the above-described antibodies.

The invention further provides a method for obtaining the described monoclonal and polyclonal antibodies.

The invention further includes the monoclonal antibodies designated as Ab1γ1 (A1), Ab2γ(mF), Ab5γ(D2), and Ab4γ (hF).

The invention also provides a hybridoma cell capable of producing the above-described monoclonal antibodies, the above-described antibodies in detectably labelled form, the above-described antibodies immobilized on a solid support.

The invention also provides a method for producing a polyclonal antibody capable of binding selectively to either mouse or human RAR-γ but not to both, which comprises the steps of:

(a) immunizing an animal with a polypeptide selected from the F region of human RAR-γ; and (b) isolating the antisera from said animal.

The invention also provides a method for producing a hybridoma cell which produces an antibody capable of binding selectively to either mouse or human RAR-γ but not to both, which comprises the steps of:

(a) immunizing an animal with a polypeptide selected from the F region of human RAR-γ;

(b) fusing the spleen cells isolated from said immunized animal with a myeloma cell;

(c) permitting the fused spleen and myeloma cells to form antibody secreting hybridoma cells; and (d) screening the hybridoma cells for a hybridoma producing an antibody which binds selectively to human RAR-γ but does not bind mouse RAR-γ.

BRIEF DESCRIPTION OF THE FIGURES

FIG. 1A: Characterization of monoclonal and polyclonal antibodies by Western blotting COS-1 cells extracts were either from control untransfected COS-1 cells (lanes 1, 4, 7, 10 and 13) or from COS-1 cells transfected with mRARγ1 (lanes 2, 3, 5, 6, 8, 9, 14, 15, 16, 18, 20 and 22), hRAR-γ1 (lanes 11 and 12) or mRAR-γ2 (lanes 17, 19, 21, and 23) expression vectors). The extracts were fractionated by SDS-PAGE, electrotransferred onto NC filters and then immunoprobed with the monoclonal antibodies Ab1γ1(A1) (lanes 1–3, 16 and 17), Ab5γ(D2) (lanes 4–6, 18-and 19), Ab2γ(mF) (lanes 1–9, 20 and 21), Ab4γ(hF) (lanes 10–12) or the rabbit polyclonal antibodies RPγ(mF) (Lanes 13–15, 22 and 23), without (lanes 1, 2, 4, 5, 7, 8, 10, 11, 13, 14, 16–23) or with previous antibody depletion (lanes 3, 6, 9, 12 and 15) as described in Materials and Methods. The position of the prestained molecular weight standards (Bethesda Research Laboratories) is indicated in kilodaltons.

FIG. 1B: Characterization of monoclonal and polyclonal antibodies by immunoprecipitation.

Figure 1A:
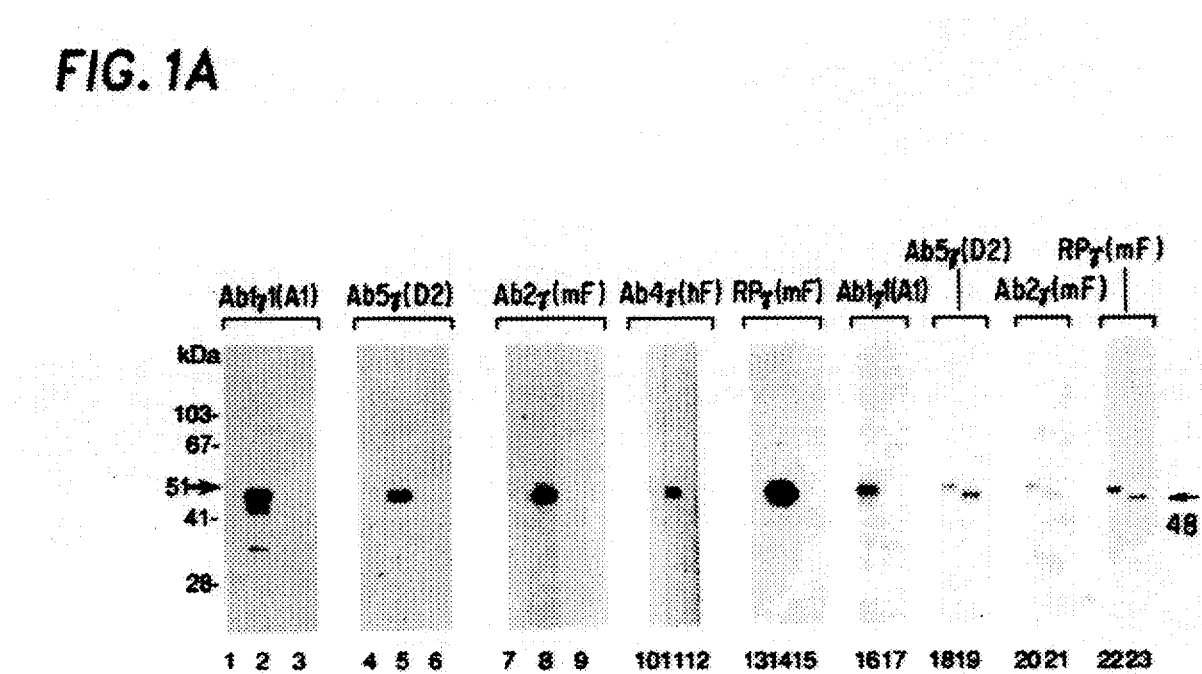
FIGS. 1A, 1B AND 1C

Extracts from either pSG5 (lanes 2–7), mRAR-γ1 (lanes 9–14), or mRAR-γ2 (lanes 17–19) transfected COS-1 cells were immunoprecipitated (as described in Materials and Methods) with the following antibodies: RPγ(mF), lanes 4 and 9; Ab1γ1(A1), lanes 5, 10 and 17; Ab5γ(D2), lanes 6, 11 and 18; Ab2γ(mF), lanes 7, 12 and 19; Non Reactive Rabbit Serum (NRS), lanes 2 and 13; Non Reactive Ascite (NRA), lanes 3 and 14. Antigen-antibody complexes bound to Protein A Sepharose beads were eluted, fractionated by SDS-PAGE, and electrotransferred to NC filters. The immunoprecipated material was immunoprobed by incubation of the filters with RPγ(mF) and [$^{125}$I] Protein A. As positive controls, extracts (10 μg protein) of mRAR-γ1 (COS-γ1, lanes 1, 8, 15 and 21) or mRAR-γ2 (COS-γ2, lanes 16 and 20) transfected COS-1 cells were directly loaded on the gel without prior immunoprecipitation, and then immunoprobed.

Figure 1B:
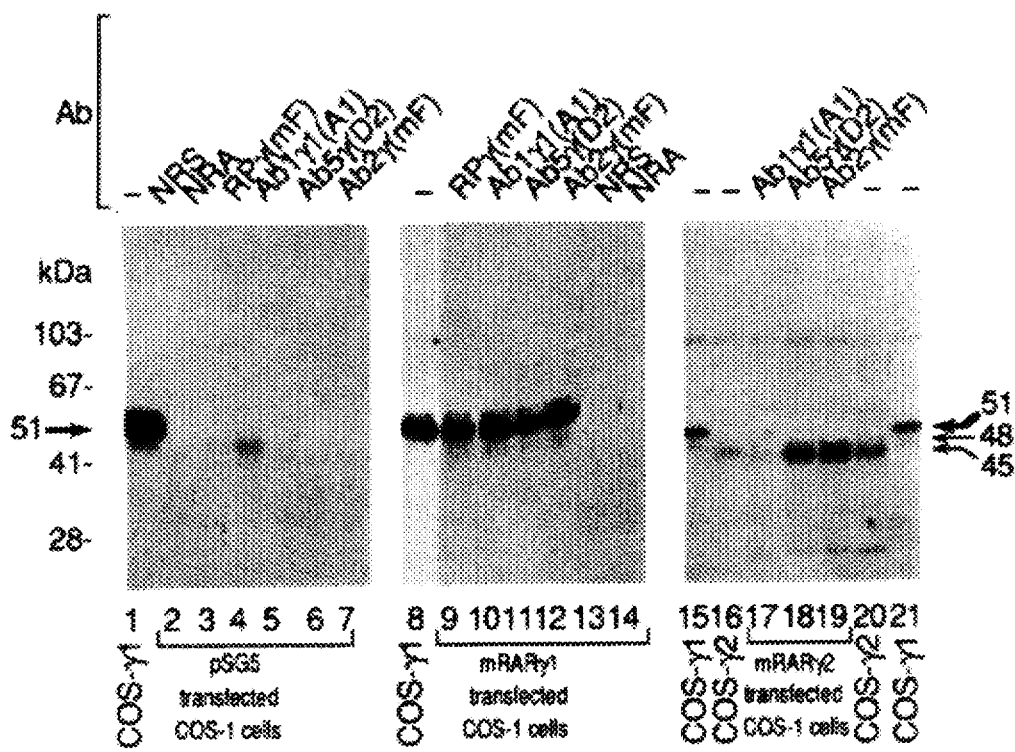
Figure 1C:
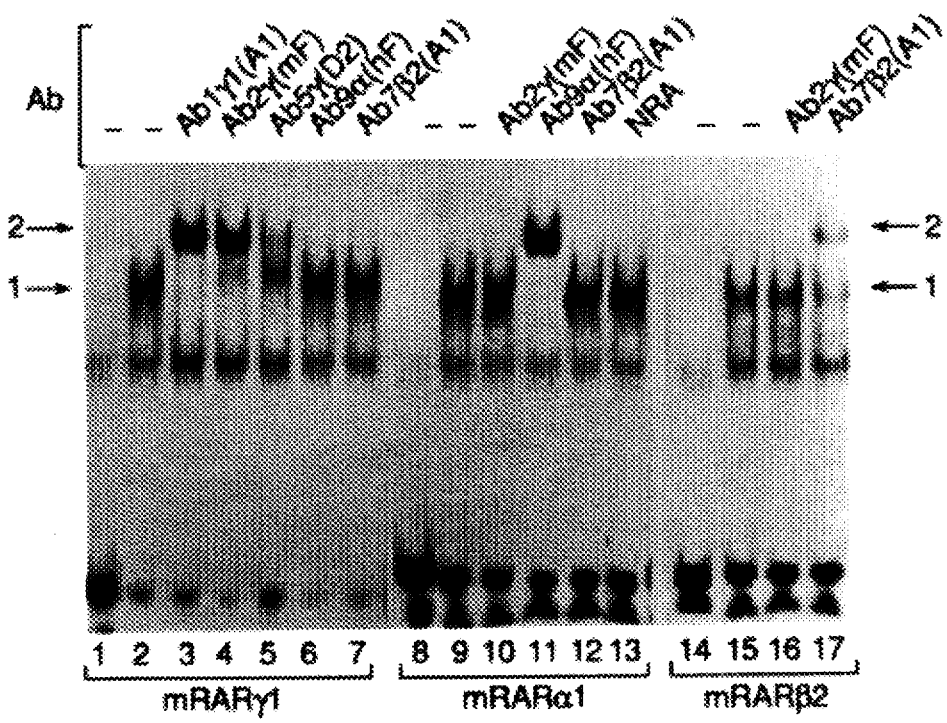

FIG. 1C: Characterization of monoclonal antibodies by their effects on the DNA-protein complexes formed in vitro with the RARE of the RAR-β2 promoter using gel retardation/shift assay.

Gel retardation reactions were carried out with 5 μg of extracts from COS-1 cells transfected with either mRAR-γ1 (lane 1–7), mRAR-α1 (lanes 8–13) or mRAR-β2 (lanes 14–17) expression vectors. Arrow 1 indicates the specific complexes formed with the RARE-β probe. Arrow 2 indicates the shifted complex formed in the presence of the monoclonal antibodies: Ab1γ1(A1), lane 3; Ab2γ(mF), lanes 4, 10 and 16;. Ab5γ(D2), lane 5; Ab9α(hF), lanes 6 and 11; Ab7β2 (A1): lanes 7, 12 and 17; Non Reactive Ascite (NRA), lane 13. The monoclonal antibodies Ab9=(hF) and Ab7β2(A1) have been raised against synthetic peptides corresponding to amino acid stretches of the F region of RAR-α1, and of the A1 region of RAR-β2, respectively.

Figure 2A:
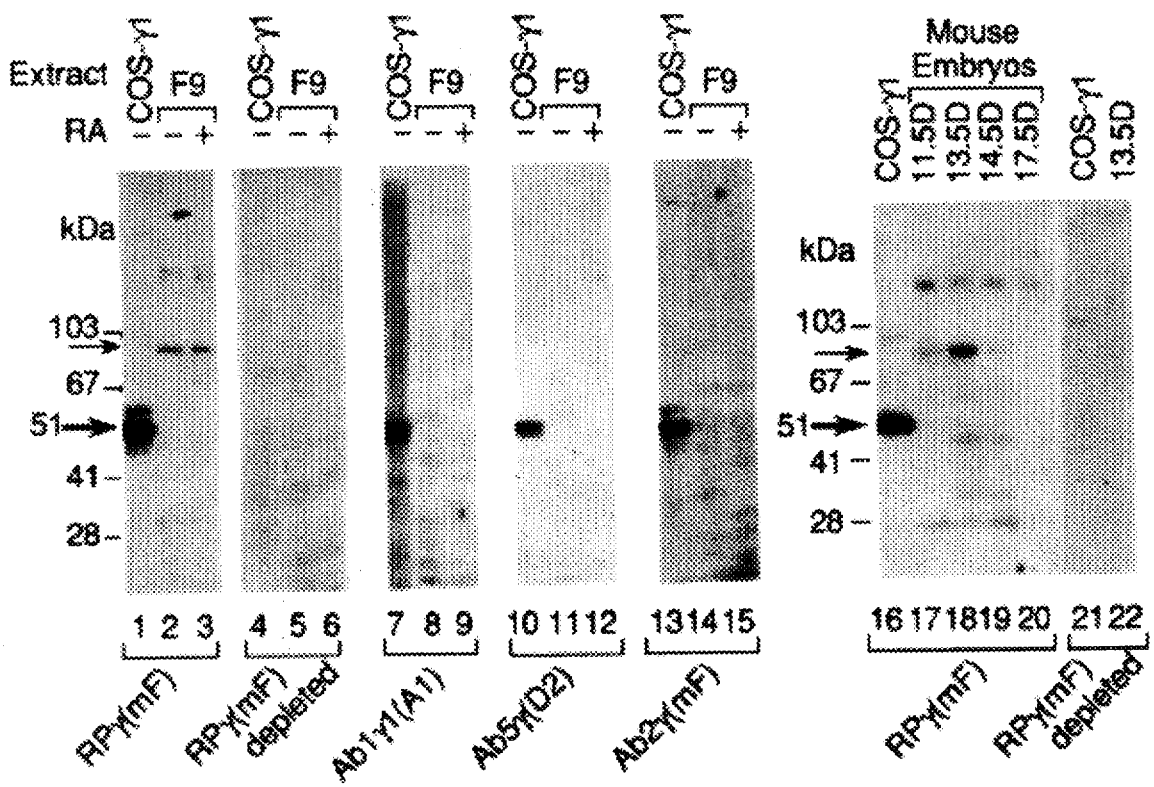
Figure 2B:
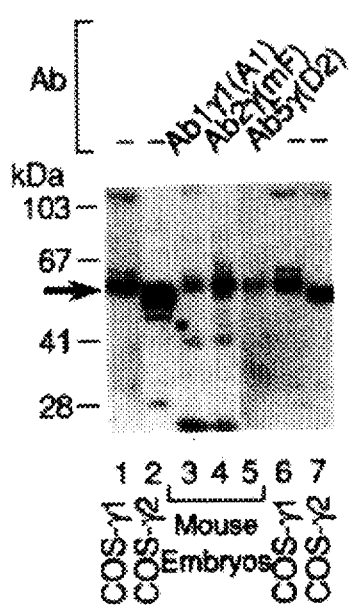
Figure 2C:
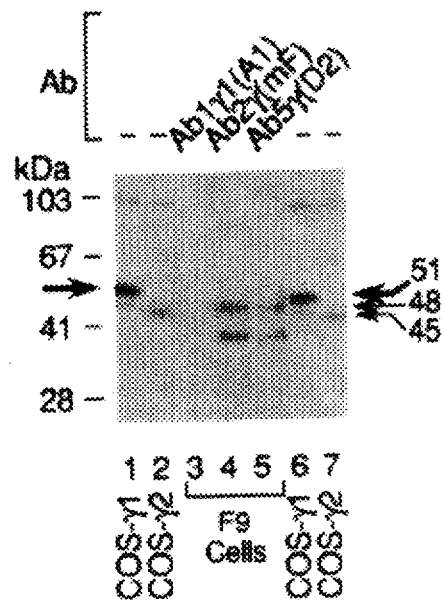

FIGS. 2A, 2B and 2C

Characterization of RAR-γ isoforms in F9 cells and mouse embryos

FIG. 2A: Immunoblotting

Nuclear extracts (70 μg protein) of F9 cells (lanes 1–15) and mouse embryos (lanes 16–22) were fractionated by SDS-PAGE, electrotransferred to NC filters and immunoprobed with: RPγ(mF), lanes 1–3, 16–20; Ab1γ1(A1), lanes 7–9; Ab5γ(D2), lanes 10–12; Ab2γ(mF), lanes 13–15. The incubations were also performed with antibody-depleted RPγ(mF) (lanes 4–6 and 21, 22). F9 cells were tested with either (lanes 3, 6, 9, 12 and 15) or without (lanes 2, 5, 8, 11 and 14) a 24 hour retinoic acid treatment. Mouse embryos were tested at 11.5 days (lane 17), 13.5 days (lanes 18 and 22), 14.5 days (lane 19) and 17.5 days (lane 20). As positive controls, extracts of mRAR-γ1 transfected COS-1 cells (COS-γ1) were run in parallel (lanes 1, 4, 7, 10, 13, 16 and 21).

FIG. 2B: Characterization of RAR-γ in mouse embryos by immunoprecipitation

Nuclear extracts (1 mg protein) of 14.5 days mouse embryos were immunoprecipitated with the monoclonal antibodies Ab1γ1(A1) (lane 3), Ab2γ(mF) (lane 4) and Ab5γ(D2) (lane 5). Antigen-antibody complexes bound to Protein A Sepharose beads were eluted, fractionated by SDS-PAGE and electrotransferred to NC filters. The immunoprecipitated mRAR-γ proteins were immunoprobed by incubation of the filters with RPγ(mF) and [$^{125}$I] Protein A. As positive controls, extracts (10 protein) of mRAR-γ1 (lanes 1 and 6) and mRAR-γ2 (lanes 2 and 7) transfected COS-1 cells were directly loaded on the gel without prior immunoprecipitation and then immunoprobed. The arrow indicates the position of mRAR-γ1.

FIG. 2C: Characterization of RAR-γ in undifferentiated F9 cells by immunoprecipitation Nuclear extracts (1 mg protein) of F9 cells were immunoprecipitated with the monoclonal antibodies Ab1γ1(A1) (lane 3), Ab2γ(mf) (lane 4), Ab5γ(D2) (lane 5). The immunoprecipitated RAR-γ proteins were immunoprobed as described in B with RPγ(mF). Extracts (10 μg protein) of mRAR-γ1 (lanes 1 and 6) or mRAR-γ2 (lanes 2 and transfected COS-1 cells were directly loaded on the gel, as positive controls. The position of the mRAR-γ1 and mRAR-γ2 controls are indicated by thick and thin arrows, respectively.

FIG. 3

Alkaline phosphatase treatment increases the electrophoretic mobility of mRAR-γ1 protein Extracts of mRAR-γ1 transfected COS-1 cells were immunoprecipitated using the Ab2γ(mF) monoclonal antibodies (lanes 3–6) and the antigen-antibody complexes immobilized on Protein-A-Sepharose beads were incubated with (lanes 5 and 6) or without (lane 4) calf intestinal alkaline phosphatase (CIP) in the absence (lanes 4 and 5) or presence (lane 6) of 10 mM sodium phosphate. The untreated (lane 3) and incubated (lanes 4–6) immunoprecipitates were then solubilized, subjected to electrophoresis and electrotransferred to NC filters. The mRAR-γ1 protein was identified by incubation of the filter with RPγ (mF) and [$^{125}$I]-Protein A. In parallel, extracts of COS-1 cells transfected with mRAR-γ1 (lanes 2 and 7) or mRAR-γ2 (lanes 1 and 8) expression vectors were run without prior immunoprecipitation.

Figure 4A:
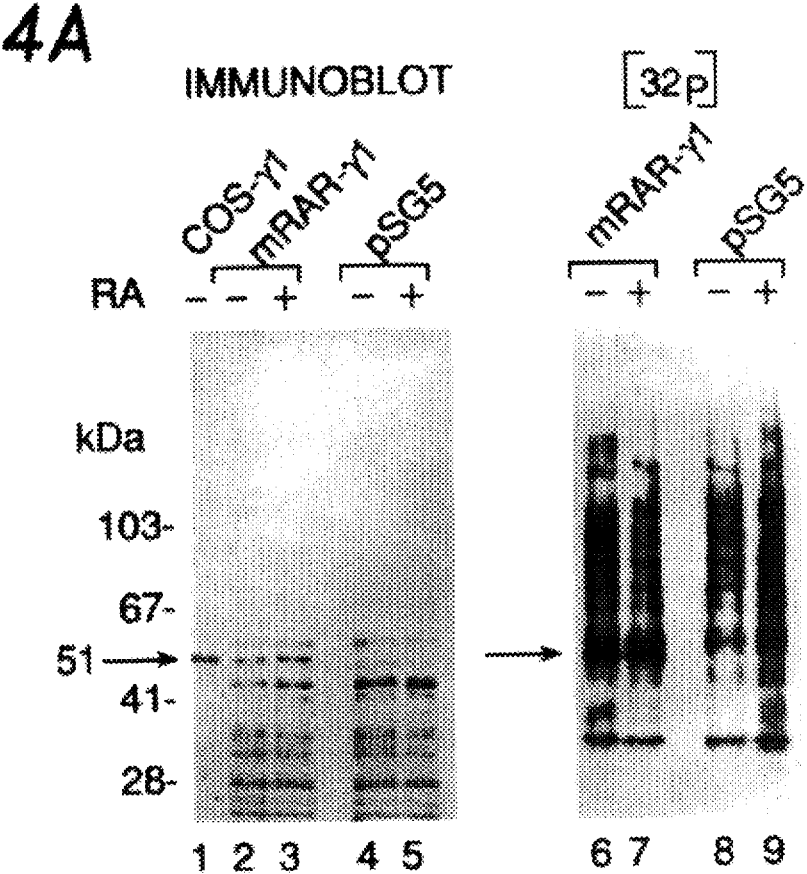
Figure 4B:
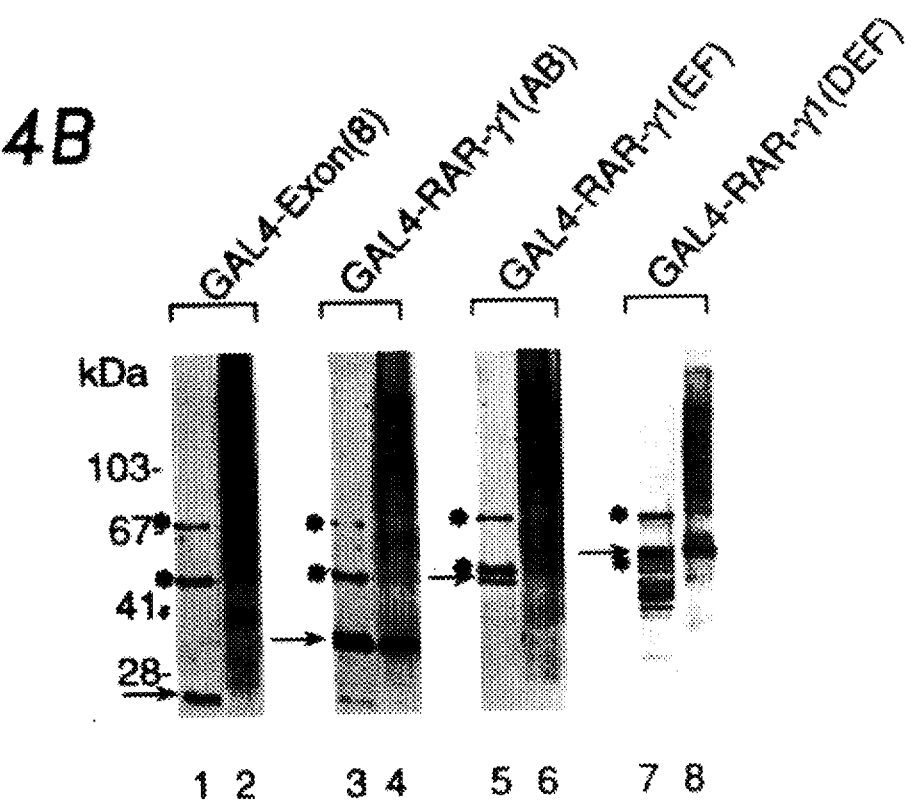

FIGS. 4A and 4B

Phosphorylation of mRAR-γ1

COS-1 cells transfected with either pSG5 (lanes 4, 5, 8 and 9) or mRAR-γ1 expression vector (lanes 2, 3, 6 and 7) were labelled with [$^{32}$P] in the presence or absence of retinoic acid (see Materials and Methods) and were analyzed by immunoprecipitation with Ab2γ(mF). After electrophoresis and electrotransfer to NC filters the immunoprecipitated phosphorylated proteins were visualized by autoradiography (lanes 6–9) and identified by incubation of the same NC filter with RPγ(mF) followed by alkaline phosphatase-labelled anti-rabbit antibodies (lanes 2–5). Extracts (10 μg protein) of mRAR-γ1 transfected COS-1 cells were run and electroblotted in parallel as a control (lane 1). FIG. 4B: COS-1 cells were transfected with the following chimeric expression vectors: GAL4-Exon(8) (lanes 1 and 2), GAL4-RAR-γ1(A/B) (lanes 3 and 4), GAL4-RAR-γ1(EF) (lanes 5 and 6), GAL4-RAR-γ1(DEF) (lanes 7 and 8). After labelling with [$^{32}$P], the extracts were immunoprecipitated with the monoclonal antibodies AbF3 (see Materials and Methods). The immunoprecipitates were eluted, subjected to electrophoresis and electrotransferred to NC filters. The phosphoproteins were analyzed by autoradiography (lanes 2, 4, 6 and 8) and identified by incubation of the same NC filter with AbF3 and revelation with alkaline phosphatase-labelled anti-mouse antibodies (lanes 1, 3, 5 and 7). The arrows indicate the position of the proteins produced by the chimeric expression vectors. Asterisks indicate contaminating immunoglobulins.

FIG. 5

Amino acid sequence (single letter code) of the synthetic peptides used to generate RAR-γ antibodies.

RAR-γ1 and RAR-γ2 (458 and 447 amino acids long proteins, respectively; same length in mouse and human) are schematically represented with their six regions designated A through F. RAR-γ1 and RAR-γ2 differ from each other only in their N-terminal A region (A1 for RAR-γ1 and A2 for RAR-γ2). The amino acid sequence (single letter code) of the synthetic peptides used to generate RAR-γ antibodies are represented. The numbers flanking the peptide sequences correspond to the portion of the respective amino acid residues in the sequence of RAR-γ isoforms. Amino acids differing between mouse and human RAR-γ are indicated.

FIG. 6

Protein kinase phosphorylation site motifs

Localization of the possible phosphorylation recognition motifs for a number of protein kinases in the amino acid sequence of A/B and D regions of RAR-γ1 (see Kemp et al., T.I.B.S. 15:342–346 (1990)) is represented. The phosphate acceptor serines are indicated with an asterisks. Where the specificity determinants for a protein kinase are known, determinant residues are underlined. Numbers indicate the position of the first amino acid in the putative recognition motif.

DESCRIPTION OF THE PREFERRED EMBODIMENTS

The present invention is based on the generation of antibodies which bind selectively to 1) either mouse of human RAR-γ but not to both, 2) antibodies which bind selectively to RAR-γ1 but not to RAR-γ2, 3) antibodies which bind selectively to the F region of both mouse and human RAR-γ, and 4) antibodies which bind selectively to the D2 region of both mouse and human RAR-γ.

The antibodies of the present invention include monoclonal and polyclonal antibodies, as well fragments of these antibodies.

The first embodiment of the present invention provides antibodies which bind selectively to either mouse or human RAR-γ but not to both.

An antibody is said to bind selectively to either mouse or human RAR-γ but not to both when the antibody is capable of binding to human RAR-γ but not to mouse RAR-γ, or, in the alternative, the antibody is capable of binding to mouse RAR-γ but not to human RAR-γ. An example of such an antibody is the mouse monoclonal antibody Ab4γ(hF). This antibody binds to human RAR-γ but not to mouse RAR-γ.

In a further embodiment, antibodies which bind selectively to RAR-γ1 but not to RAR-γ2 are disclosed. Such antibodies will bind to RAR-γ1 but not to RAR-γ2. An example of such an antibody is the mouse monoclonal antibody Ab1γ1(A1).

In a further embodiment, antibodies which bind selectively to the F region of both mouse and human RAR-γ are disclosed. Such antibodies will bind only the F region of RAR-γ and will not bind other regions of RAR-γ. An example of such an antibody is the mouse monoclonal antibody Ab2γ(mF).

In a further embodiment, antibodies which bind selectively to the D2 region of both mouse and human RAR-γ are disclosed. Such antibodies will bind only the D2 region of RAR-γ and will not bind other regions of RAR-γ. An example of such an antibody is the mouse monoclonal antibody Ab5γ(D2).

Additionally, the present invention includes humanized forms of the antibodies disclosed herein. The humanized antibodies of the present invention may be generated using one of the procedures known in the art such as chimerization or CDR grafting.

In another embodiment of the present invention, the above-described antibodies are detectably labelled. Antibodies can be detectably labelled through the use of radioisotopes (such as $^{125}I$ or $^{14}C$, etc.), affinity labels (such as biotin, avidin, etc.), enzymatic labels(such as horse radish peroxidase, alkaline phosphatase, etc.) fluorescent labels (such as FITC or rhodamine, etc.), paramagnetic atoms, etc. Procedures for accomplishing such labelling are well-known in the art, for example see Sternberger, L. A. et al., J. Histochem. Cytochem 18:315 (1970), Bayer, E. A. et al., Meth. Enzym. 62:308 (1979), Engval, E. et al., Immunol. 109:129 (1972), Goding, J. W. J. Immunol. Meth. 13:215 (1976).

In another embodiment of the present invention the above-described antibodies are immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir, D. M. et al., "Handbook of Experimental Immunology" 4th Ed., Blackwell Scientific Publications, Oxford, England, Chapter 10 (1986), Jacoby, W. D. et al., Meth. Enzym. 34 Academic Press, N.Y. (1974).

The invention also provides hybridomas which are capable of producing the above-described antibodies. A hybridoma is an immortalized cell line which is capable of secreting a specific monoclonal antibody. An example of such a hybridoma cell line include the 11B11 (HB188) and J11d.2 (TIB183) cell lines which have been deposited at the ATCC depository.

In another embodiment of the present invention, a method of identifying expression of RAR-γ, or a specific isoform of RAR-γ, in test sample is presented. The test samples of the present invention include cells, protein or membrane extracts of cells, or biological fluids such as blood, serum, plasma, or urine. Any cell or tissue can be used as a test sample, however the most preferred test samples are obtained from skin cells.

Specifically, the method provides a procedure which identifies whether a test sample contains RAR-γ or one of the specific isoforms of RAR-γ.

In detail, the method comprises incubating a test sample with one of the previously-described antibodies and assaying whether the antibody binds to the test sample. Conditions for incubating an antibody with a test sample vary. Incubating conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based ouchterlony, or rocket immunofluorescent assays) can readily be adapted to employ the antibodies of the present invention. Examples of such assays can be found in Chard, T. "An Introduction to Radioimmunoassay and Related Techniques" Elsevier Science Publishers, Amsterdam, The Netherlands (1986); Bullock, G. R. et al., "Techniques in Immunocytochemistry," Academic Press, Orlando, Fla. Vol. 1 (1982), Vol. 2 (1983), Vol. 3 (1985); Tijssen, P., "Practice and Theory of Enzyme Immunoassays: Laboratory Techniques in Biochemistry and Molecular Biology," Elsevier Science Publishers, Amsterdam, The Netherlands 1985).

The test sample used in the above-described method will vary based on the assay format, nature of the detection method and the tissues, cells or extracts used as the sample to be assayed. Most preferably, the test sample will be derived from skin tissues or cells. Methods for preparing protein extracts or membrane extracts of cells are well known in the art and can be readily be adapted in order to obtain a sample which is capable with the system utilized.

In a further embodiment of the present invention, methods are provided for preparing a monoclonal antibody which binds selectively to 1) either human or mouse RAR-γ, but not to both, 2) RAR-γ1 but not to RAR-γ2, 3) the F region of both mouse and human RAR-γ, and 4) the D2 region of both mouse and human RAR-γ.

In general, techniques for preparing monoclonal antibodies are well known in the art (Campbell, A. M., "Monoclonal Antibody Technology: Laboratory Techniques in Biochemistry and Molecular Biology," Elsevier Science Publishers, Amsterdam, The Netherlands (1984); St. Groth et al., J. Immunol. Methods 35:1–21 (1980).

In the preferred method for generating an antibody which binds selectively to human RAR-γ but not to mouse RAR-γ, a polypeptide is chosen whose amino acid sequence is obtained from the F region of human, RAR-γ such that the peptide contains at least one amino acid residue which differs from the corresponding sequence of the F region of mouse RAR-γ as the antigen to be used in immunizing an animal. The most preferred peptide for generating such an antibody is the SP25 peptide whose amino acid sequence is as follows: QPGPHPNASSEDEV (SEQ ID. NO. 1).

In detail, an animal (mouse, rabbit, etc.) is immunized with the selected polypeptide. Methods for immunization are well known in the art. Such methods include subcutaneous or interperitoneal injection of the polypeptide. One skilled in the art will recognize that the amount of polypeptide used for immunization will vary based on the animal which is immunized, the antigenicity of the polypeptide and the site of injection. The polypeptide may be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al., Exp. Cell Res. 175:109–124 (1988)).

Hybridomas secreting the desired antibodies are cloned and the class and subclass is determined using procedures known in the art (Campbell, A. M., Monoclonal Antibody Technology: Laboratory Techniques in Biochemistry and Molecular Biology, Elsevier Science Publishers, Amsterdam, The Netherlands (1984)).

For polyclonal antibodies, antibody containing antisera is isolated from the immunized animal and is screened for the presence of antibodies with the desired specificity using one of the above-described procedures.

In the preferred method for generating an antibody which binds selectively to RAR-γ1 but not to RAR-γ2, a polypeptide is chosen whose amino acid sequence is obtained from the A1 region of RAR-γ1, such that the amino acid sequence of the A region contains at least one amino acid residue which differs from the corresponding sequence of the A2 region of RAR-γ2 as the antigen to be used in immunizing an animal as described above. The most preferred peptide for generating such an antibody is the SP15 polypeptide whose amino acid sequence is as follows: selectively to the F region of both mouse and human RAR-γ, a FEHLSPS-FRGLG. (SEQ. ID. NO. 2).

In the preferred method for generating an antibody which binds polypeptide is chosen whose amino acid sequence is obtained from the F region of RAR-γ, such that the amino acid sequence of the peptide contains amino acid residues which are common to both the mouse and human RAR-γ F region, but differs in sequence by at least one amino acid from the other regions of the receptor, as the antigen to be used in immunizing an animal as described above. The most preferred peptide for generating such an antibody is the SP14 polypeptide whose amino acid sequence is as follows: SSEDEAPGGQGKRGQS. (SEQ. ID. NO. 3).

In the preferred method for generating an antibody which binds selectively to the D2 region of both mouse and human RAR-γ, a polypeptide is chosen whose amino acid sequence is obtained from the D2 region of RAR-γ, such that the amino acid sequence of the peptide contains amino acid residues which are common to both the mouse and human RAR-γ $D_2$ region, but differs in sequence by at least one amino acid from the other regions of the receptor, as the antigen to be used in immunizing an animal as described above. The most preferred peptide for generating such an antibody is the SP81 polypeptide whose amino acid sequence is as follows: KEEGSPDSYELS. (SEQ. ID. NO. 4).

One skilled in the art will readily recognize that the above-described procedures can be utilized not only for generating an antibody which binds selectively to RAR-γ1 but not to RAR-γ2, but also can be used as well to generate an antibody which binds selectively to RAR-γ2 and not to RAR-γ1 or which binds selectively to any of the other specific subtype of RAR-γ. Specifically, an individual wishing to generate an antibody with a desired specificity first analyzes the sequences of the various RAR-γ's disclosed in Krust et al., Proc. Natl. Acad. Sci. USA 86:5310–5314 (1989), Giguère et al. Mol. Cell. Biol. 10:2335–2340 (1990), Kastner et al., Proc. Natl. Acad. Sci. USA 87:2700–2704 (1990), second, chooses a peptide sequence from the desired isotype which differs by at least one amino acid in the corresponding sequence from the other RAR-γ isoforms, and then uses the .peptide sequence as a immunogen as described previously.

In another embodiment of the present invention, a kit is provided which contains all the necessary reagents to carry out the previously described assays.

Specifically, the invention provides a compartmentalized kit to receive, in close confinement, one or more containers which comprises: (a) a first container comprising one of the following antibodies: an antibody which binds selectively to either mouse of human RAR-γ but not to both, an antibody which binds selectively to RAR-γ1, but not to RAR-γ2, an antibody which binds selectively to the F region of either mouse or human RAR-γ, or an antibody which binds selectively to the D2 region of RAR-γ and (b) one or more other containers comprising one or more of the following: wash reagents and reagents capable of detecting presence of bound antibodies from the first container.

In detail, a compartmentalized kit includes any kit in which reagents are contained in separate containers. Such containers include small glass containers, plastic containers or strips of plastic or paper. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the antibodies used in the assay, containers which contain wash reagents (such as phosphate buffered saline, Tris-buffers, etc.), and containers which contain the reagents used to detect the bound antibody.

Types of detection reagents include labelled secondary antibodies, or in the alternative, if the primary antibody is labelled, the chromophoric, enzymatic, or antibody binding reagents which are capable of reacting with the labelled antibody. One skilled in the art will readily recognize that the disclosed antibodies of the present invention can readily be incorporated into one of the established kit formats which are well known in the art.

In another embodiment of the present invention a method is provided for identifying compounds which interact with a specific type or a subset of the RAR receptors.

In detail, cells or tissues are incubated with a test compound alone and in the presence of one or more of the antibodies of the present invention or co-pending application U.S. Ser. No. 07/646,527 (herein incorporated by reference). The binding of the test compound can be monitored either directly or indirectly. The level of binding with and without antibodies present is determined. By comparing the level of binding each of the various antibodies inhibit, one can determine the receptors utilized by the test compound.

Having now generally described the invention, the agents and methods of obtaining same will be more readily understood through reference to the following examples which are provided by way of illustration, they are not intended to be limiting of the present invention unless specified.

EXAMPLES

MATERIALS AND METHODS

DNA constructs

The plasmids containing the mouse or human RAR gene coding sequences RAR-α1, RAR-β2 and RAR-γ1 (previously referred to as RAR-α0, RAR-β0 and RAR-γ0 respectively), were described (Petkovich et at, Nature 330:444–450 (1987); Brand et al., Nature 332:850–853 (1988); Krust et at, Proc. Natl. Acad. Sci. USA 86:5310–5314 (1989); Zelent et al., Nature 339:714–717 (1989)). The construction of the isoform mRAR-γ2 expression vector has been reported (Kastner et al., Proc. Natl. Acad. Sci. USA 87:2700–2704 (1990)).

The GAIA/RAR-γ1(A/B) chimera was constructed by replacing the human estrogen receptor (hER) exon 7 in the vector GAL4-Exon7-F (Webster et at., EMBO J. 8:1441–1446 (1989)) with a 265 bp Xho-KpnI fragment encoding amino acids 1–89 of mRAR-γ1 (A/B region). Amino acids in the linker between GAL4 (1–147) and the RAR-γ1 A/B region are IGRPPRA. The GAL4-RAR-γ(EF) and (DEF) constructs were made similarly by replacing hER exon 7 with a 782 bp XhoI-KpnI fragment (amino acids 201–458 of mRAR-γ1) and a 917 bp XhoI-KpnI fragment) (amino acids 156–458 of mRAR-γ1) respectively. GAL4-RAR-γ(EF) and (DEF) chimeras also contain the amino acids IGRPPRA in the linker region. The mRAR-γ1 XhoI-KpnI cassettes were obtained from mRAR-γ1 clones that had been modified by two rounds of site directed mutagenesis to introduce XhoI and KpnI restriction sites at selected positions. Each of the three chimeric constructs encodes amino acids 553–595 of hER (F region) as a carboxyl terminal antigenic tag against which monoclonal antibodies (AbF3) have been raised (Rochette-Egly et al., Genes Develop. 4:137–150 (1990)).

Cull Culture and Transfection

COS-1 cells were grown in 9cm diameter Petri dishes, in Dulbecco's modified Eagle medium, containing 5% fetal calf serum, 500 units penicillin, 400 µg gentamicin and 100 µg streptomycin per milliliter. Culls were transfected by using the calcium phosphate technique as previously described (Brand et al., Nature 332:850–853 (1988)). Transfections included either the mouse RAR-γ1, γ2, α1 or β2 expression vectors (5 µg) and plasmid carrier DNA (Bluescribe) in order to adjust the total DNA quantity to 20 µg per dish. F9 EC cells were grown and treated with retinoic acid ($10^{-7}$M) for 24 h where indicated.

Synthesis of peptides, preparation of antisera and monoclonal antibodies

Figure 5:
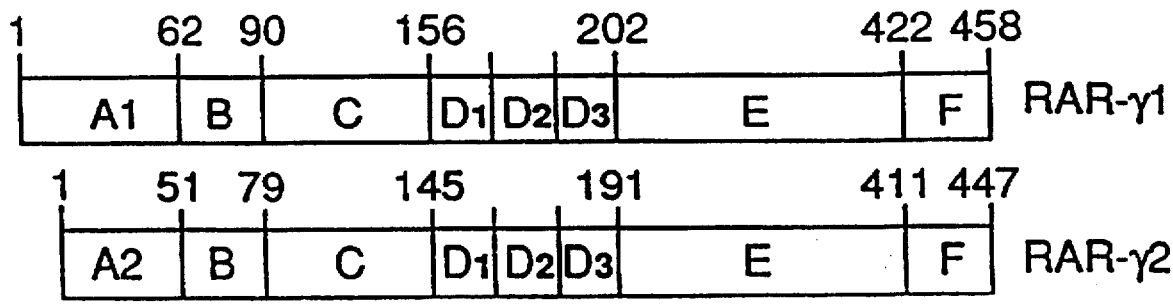

The synthetic peptides SP15(A1 region of mouse or human RAR-γ1), SP14 (F region of all mRAR-γ isoforms), SP81 (D2 region of all human and mouse RAR-γ isoforms) and SP25 (F region of all hRAR-γ isoforms (see FIG. 5) deduced from the cDNA of human and mouse RAR-γ1 were synthesized in solid phase using Fmoc chemistry (ABI model 431A peptide synthesizer), verified by amino acid analysis (analyzer ABI 420A- 20A-130A system) and coupled to ovalbumin (Sigma) through an additional $NH_2$-extraterminal cysteine residue, using bifunctional reagent MBS (Aldrich).

Rabbit immunization and antisera preparation have been previously described (Gaub et al., Proc. Natl. Acad. Sci. USA 86:3089–3093 (1989)). For monoclonal antibodies preparation, eight week-old female Balb/c mice were injected intraperitoneally with 100 µg of coupled antigens. Four days before the fusion, positive mice received a booster injection of antigen (100 µg), and then 10 µg (intravenous and interperitoneal route) every day until spleen removal. The spleen cells were fused with Sp2/0-Ag14 myeloma cells essentially according to St. Groth and Scheidegger (1980) (St. Groth et al., J. Immunology Methods 35:1–21 (1980). Culture supernatants were screened by ELISA using the unconjugated peptide as antigen. Positive cultures were then tested by immunofluorescence and Western blotting on RAR-γ1 cDNA-transfected COS-1 cells as described by Lutz et al. (1988) (Lutz et al., Experimental Cell Research 175:109–124 (1988)). Hybridomas secreting antibodies recognizing specifically RAR-γ1 were cloned twice on soft agar. Each hybridoma was also adapted in serum-free medium SFRI-4 (SFRI, France). For ascite fluid production, $2 \times 10^6$ cells were injected in pristine-primed Balb/c mice. Class and sub-class determination was performed using an Isotyping Kit (Amersham). Both SFRI culture supernatants and ascite fluids were used as monoclonal antibody sources.

Preparation of whole cell and nuclear extracts from cultured cells and mouse embryos Whole cell extracts (WCE) were prepared from confluent transfected cultures of COS-1 cells. Cells were washed with chilled PBS, centrifuged. The pellet was homogenized at 4° C. with a glass Dounce B homogenizer (20 pestle strokes) in 2 volumes of 10 mM Tris-HCl pH8, containing 20 mM sodium molybdate, 0.6M KCl, 1.5 mM EDTA, 1 mM PMSF and PIC (protease inhibitor cocktail: leupeptin, aprotinin, pepstatin, antitrypsin and chymostatin at 0.5 µg/ml each). After centrifugation for 1 hour at 105,000xg and 4° C., the supernatant was concentrated by ultrafiltration through ten-triton 30 microconcentrators (Amicon, USA). Glycerol was added to 25% final concentration and the extracts were aliquoted and kept at −80° C. For the preparation of nuclear extracts (NE), the washed cells were first lysed at 4° C. with a glass Dounce B homogenizer (15 strokes) in Buffer A (20 mM Tris-HCl pH8, 1 mM MgCl$_2$, 20 mM KCl, 1 mM DTT, 0.3 mM PMSF, PIC). After centrifugation for 5 min at 1500xg at 4° C., the crude nuclear pellet was washed-twice, resuspended in high salt buffer B (same as buffer A but with 0.6M KCl and 25% glycerol) and homogenized with Dounce B (20–30 strokes). Extraction of nuclear proteins was performed on ice under gentle vortexing. After centrifugation for 1 hour at 105,000xg, the supernatant was concentrated by using microconcentrators (see above), aliquoted and frozen in liquid nitrogen.

Mouse embryos were collected at 11.5, 13.5, 14.5 and 17.5 days post-coitum (p.c.) and nuclear extracts were prepared, according to the same protocol except that the crude nuclear pellet was further purified in some cases by centrifugation on a 1.7M sucrose cushion (30 minutes at 1500 g) and was recovered at the interphase. Proteins were quantified by the method of Bradford (1976) (Bradford, M. M., Anal. Biochem 72:248–254 (1976)).

Immunoblotting

Protein (10–70 µg) from either whole cell or nuclear extracts were fractionated by SDS-PAGE (10% polyacrylamide), electrotransferred onto a nitrocellulose (NC) filter as described (Gaub et al., Proc. Natl. Acad. Sci. USA 86:3089–3093 (1989)) and immunoprobed as follows. The NC filters were "blocked" in PBS-3% non-fat powdered milk, and then incubated for 2 hours at 37° C. with either rabbit polyclonal or mouse monoclonal antibodies at the required dilution in PBS. After extensive washing in PBS containing 0.05% Tween 20 and washing in PBS-0.3% non-fat powdered milk, the filters were incubated for 90 minutes at 20° C. with either [$^{125}$I]-labelled Protein A or [$^{125}$I]-labelled goat anti mouse immunoglobulins (Amersham). After extensive washing with PBS/Tween 20, the filters were dried and autoradiographed. When mentioned, alkaline phosphatase-coupled immunoglobulins (goat anti-rabbit or anti-mouse immunoglobulins, Jackson Immuno Research) were used and staining was performed by using the NBT/BCIP substrate kit (Pierce).

The specificity of the reaction was checked by depleting the antisera from the specific antibodies by incubation with nitrocellulose (NC) filter dotted with the coupled peptide (20 µg).

Gel retardation assay

Mobility shift assays were performed as in Garner and Revzin (1981) (Garner et al., Nucl. Acids Res. 9:3047–3060 (1981)) using the wild type and mutated double-stranded oligodeoxynucleotides (RARE-β and RARE-βm, respectively) corresponding to the RARE of the RARβ gene (de Thè et al., Nature 343:177–180 (1990)) as described in Nicholson et al. (1990) (Nicholson et al., EMBO J. 9:4443–4454 (1990)). Nuclear extract, usually 5 µg protein, was incubated in 20 µl reaction mixture containing 20 mM TRIS HCl, pH 7.5, 100 mM KCl, 1 mM MgCl$_2$, 0.1 mM EDTA, 0.5 mM DTT, 10% glycerol, 4 µg poly(dI-dC) and 0.2 ng (≈20 000 cpm) double stranded [$^{32}$P]-5'-end labelled synthetic RARE oligodeoxynucleotide and, when requested, 1 µl of ascite fluid antibodies (diluted ⅓). Poly(dI-dC) and nuclear extract were first incubated at 4° C. for 15 minutes before adding the labelled oligodeoxynucleotide. After a further 15 minute incubation on ice, the antibodies were added when requested, and the mixture reaction was maintained on ice for 15 minutes before loading the gel. Free DNA and DNA-protein complexes were resolved on a 5% polyacrylamide gel in 0.5×TBE (45 mM Tris-base, 45 mM Boric acid, 2 mM EDTA).

Immunoprecipitations

The cell extracts (50 µg protein) were first preabsorbed with non-immune serum or control ascite fluid in a 1 ml final volume of 10 mM Tris-HCl, pH 7.5, 1 mM EDTA, 0.1% Triton X100 (Buffer C) with constant agitation at 4° C. for 1 hour. Then Protein A Sepharose CL-4B beads (Pharmacia, Upsala, Sweden) were added (100 µl of a 50% V/V slurry in Buffer C) for a further one hour incubation. The "absorbed" extract, which was recovered in the supernatant after pelleting by centrifugation the non relevant protein-IgG-Protein A Sepharose complexes, was incubated with 3 µl of immune serum or ascite fluid for 1 hour at 4° C. When using monoclonal antibodies (IgG1 kappa) a further 1 hour incubation with a rabbit anti-mouse IgG fraction (1.81 µg, Jackson Immuno Research) was required as a bridge. Protein A Sepharose beads were then added for one hour at 4° C. After centrifugation, the pellet was washed four times with Buffer C. Antigen-antibody complexes were eluted by incubation at 100° C. for 10 minutes in 50 µl of electrophoresis sample buffer (50 mM Tris-HCl pH6.8, 2% SDS, 10% glycerol, 100 mM β-mercaptoethanol and 0.001% bromophenol blue). Immunoblotting was then performed as described above.

Alkaline phosphatase treatment of immunoprecipitates

Immunoprecipitates were suspended in 100 µ phosphatase reaction mixture containing 100 mM Tris-HCl buffer (pH 9.8), 1 mM MgCl$_2$, 0.1 mM ZnCl$_2$, PIC, and 20 units of calf intestinal alkaline phosphatase (Boehringer, Mannheim). Sodium phosphate 10 mM was included as indicated. Incubation was performed at 37° C. for 3 hours followed by centrifugation, washing, addition of electrophoresis sample buffer, heating, electrophoresis and immunoblotting.

Phosphate Labelling 24 hour transfected COS-1 cells were first starved overnight in Dulbecco's modified Eagle medium deficient in phosphate, and then labelled with [$^{32}$P]-(1mCi/2 ml, ≈2.10$^6$ cells) for 4 hours at 37° C. Cell monolayers were washed 6 times in ice-cold PBS and lysed by 5 successive freezings (at −80° C.) and thawings in buffer A. After centrifugation at 8000×g for 20 minutes at 4° C., the supernatant was subjected to immunoprecipitation as described above. Proteins from the immune complexes were eluted, separated by SDS-PAGE electrophoresis and electrotransferred to NC filters. The phosphorylated proteins were visualized by autoradiography. Proteins were identified as mRAR-γ by incubation of the same filter with specific antibodies followed by an alkaline phosphatase-labelled second antibody as described above.

RESULTS

A) Preparation of polyclonal and monoclonal antibodies against synthetic peptides specific to human and mouse RAR-γ isoforms RAR-γ1 and γ2 isoforms which differ from each other only in their N-terminal A regions (A1 for RAR-γ1 and A2 for RARγ2) are highly conserved between mouse and human, both in their length which is identical, and in their amino acid sequences which are very similar with the exception of the very C-terminal region (Krust et al., Proc. Natl. Acad. Sci. USA 86:5310–5314 (1989); Kastner et al., Proc. Natl. Acad. Sci. USA 87:2700–2704 (1990); see also FIG. 5). The main differences between RAR-γ isoforms and RAR-α and β isoforms are located in the N-terminal A region, central D2 region, and carboxy terminal F region (Zelent et al., Nature 339:714-717 (1989); Krust et al., Proc. Natl. Acad. Sci. USA 86:5310-5314 (1989); Kastner et al., Proc. Natl. Acad. Sci. USA 87:2700-2704 (1990)). Thus in order to obtain specific antibodies corresponding to known epitopes, potential immunogenic amino acid sequences which were either specific to all RAR-γ isoforms (regions D2 and F) or unique to RAR-γ1 (region A1) (see FIG. 5) were selected. Two of these peptides (SP15 and SP81, corresponding to regions A1 and D2, respectively) are fully conserved between human and mouse, whereas the two others (SP25 and SP14, corresponding both to region F) diverge by 3 or 4 amino acids.

The four peptides were antigenic in mice and resulted in the production of specific hybridomas. Based on the intensity of the reaction obtained by immunoblotting and immunoprecipitation, one clone corresponding to each peptide was selected: SP15 [Ab1γ1(A1)], SP14 [Ab2γ(mF)], SP25 [Ab4γ(hF)] and SP81 [Ab5γ(D2)]. Each clone recognized specifically its cognate, but not other peptides, as checked by ELISA (data not shown). All four antibodies were identified as IgG1 kappa. Peptides SP14, SP15 and SP25 resulted also in the production of polyclonal antibodies in rabbits, but only the polyclonal antibody preparation against SP14 [RPγ(mF)] which gave the strongest reaction was further studied.

B) Specific detection of cloned human and mouse RAR-γ proteins by immunoblotting, immunoprecipitation and gel shift assay 1. Immunoblotting The monoclonal antibodies as well as the rabbit polyclonal antisera were tested for their ability to reveal specifically on Western blots the cloned mouse or human RAR-γ proteins produced by transfected COS-1 cells (see Materials and Methods). Whole cell extracts (WCE) of COS-1 cells transfected with vectors expressing either the human or mouse RAR-γ1 isoform were fractionated by SDS-PAGE and electroblotted on to nitrocellulose (NC) filters. After incubation of the filters with the specific monoclonal antibodies or the rabbit antisera, antibody-antigen complexes were revealed by using [$^{125}$I]-anti-mouse immunoglobulins or [$^{125}$I]-Protein A respectively (FIG. 1A).

In extracts of COS-1 cells transfected with mRAR-γ1 expression vector, the monoclonal antibodies Ab1γ1(A1), Ab5γ(D2) and Ab2γ(mF), as well as the SP14 rabbit antiserum RPγ(mF), resulted in a specific strongly labelled signal with an apparent molecular mass of ≈51 kDa (FIG. 1A, lanes 2, 5, 8, 14), which is in excellent agreement with the cDNA deduced molecular mass of the mRAR-γ1 protein (Mr=50,347; Krust et al., Proc. Natl. Acad. Sci. USA 86:5310-5314 (1989)). It must be noted that a specific additional signal with a lower apparent molecular mass and variable intensity depending on the cell extract was detected with the monoclonal Ab1γ1 (A1)(FIG. 1A, lane 2; see also FIG. 2A, lane 7). Similarly, with monoclonal Ab2γ(mF) and polyclonal RPγ(mF), a specific additional minor signal with a higher apparent molecular weight (and variable intensity) was seen (FIG. 1A, lanes 8 and 14; see also FIG. 2A, lanes 1 and 13). No labelling was detectable with the monoclonal antibody Ab4γ(hF) (data not shown). In hRAR-γ1-transfected COS-1 cells extracts, a similar specific 51 kDa signal was also revealed by Western blotting with Ab1γ1 (A1), Ab2l(γ(mF) and Ab5γ(D2) (data not shown), as well as with Ab4γ(hF) (FIG. 1A, lane 11). However, the RPγ(mF) antiserum did not recognize the human cloned receptor (data not shown).

When the ascite fluids and the antisera were depleted from the specific antibodies as described in Materials and Methods, all of the above specific signals were no longer seen (FIG. 1A, lanes 3, 6, 9, 12, 15). Similar competition experiments using ovalbumin alone did not affect the intensity of the specific signals (dam not shown). No specific labelling was observed on Western blots performed with extracts of untransfected COS-1 cells (FIG. 1A, lanes 1, 4, 7, 10, 13), suggesting a very low level of expression of RAR-γ1 protein in these cells. Furthermore, no cross-reactions were seen with the same antibodies using extracts from COS-1 cells transfected with either mouse or human RAR-α1 or mouse or human RAR-β2 (data not shown), indicating that the present antibodies are specific for the RAR-γ1 protein. However, as expected, Ab5γ(D2), Ab2γ(mF) and RPγ(mF) reacted also specifically with extracts from mRAR-γ2 transfected COS-1 cells and revealed a protein with an apparent molecular weight of ≈48 kDa. (FIG. 1A, lanes 19, 21, 23). In some instances the 48 kDa species was strongly decreased in favor of a specifically reactant protein with an apparent molecular weight of ≈45 kDa (see for instance FIG. 1B, lanes 16 and 22; FIG. 2B, lane 5 and FIG. 2C, lanes 2 and 9). In contrast, the mRAR-γ2 protein present in these extracts was not recognized by Ab1γ1(A1), in agreement with the presence of a different A region (A2) in the mRAR-γ2 isoform (see above) (FIG. 1A, lane 17).

These results demonstrate that the monoclonal antibodies Ab2γ(mF) and Ab5γ(D2) recognize specifically the corresponding epitopes present in both human and mouse RAR-γ proteins, whereas the AB4γ(hF) antibody recognizes specifically the corresponding epitope present in hRAR-γ isoforms. Conversely, the polyclonal antiserum RPγ (mF) recognizes only the corresponding epitope present in mouse RAR-γ isoforms. These results show also that the monoclonal antibody Ab1γ1(A1) reacts specifically with the corresponding epitope which is present in human and mouse RAR-γ1 isoform, but not in human and mouse RAR-γ2 isoform.

2. Immunoprecipitation

The three monoclonal antibodies [Ab1γ1(A1), Ab2γ(mF) and Ab5γ(D2)] as well as RPγ(mF) also specifically immunoprecipitated mRAR-γ1 protein from whole cell extracts of mRAR-γ1-transfected COS-1 cells (FIG. 1B), as shown by subsequent Western blotting (FIG. 1B, lanes 9-12). As expected (see above), no specific signal was seen when extracts from mRAR-γ2-transfected cells were immunoprecipitated with Ab1γ1(A1) (FIG. 1B, lane 17), whereas signals were observed when using the same extracts and either Ab5γ(D2) or Ab2γ(mF) (FIG. 1B, lanes 18 and 19). Also, as expected RPγ(mF) did not immunoprecipitate hRAR-γ1 from extracts of hRAR-γ1 -transfected cells, whereas Ab4γ(hF) did it but with a lower efficiency than Ab1γ1(A1) or Ab5γ(D2) or Ab2γ(mF) (data not shown). In all cases the signals were specific, since they were not observed when immunoprecipitation was performed with pre-immune non-reactive serum (NRS) or a control non reactive ascite fluid (NRA) (FIG. 1B, lanes 13 and 14)or with cell extracts transfected with the parental expression vector pSG5 (FIG. 1B, lanes 4-7). Furthermore, the signals disappeared specifically when the Western blotting step was performed with an antibody-depleted ascite fluid or serum (data not shown). A minor signal corresponding to the immunoprecipitating rabbit immunoglobulin was occasionally revealed (data not shown, and FIG. 1B, lane 4).

3. Gel shift assay

In order to confirm the specificity of the present antibodies for the RAR-γ isoforms, gel shift/retardation assays were performed using a [$^{32}$P] labelled oligodeoxynucleotide (RARE-β, see Materials and Methods) containing the RA response element (RARE) of the RAR-β promoter (de Thèet al., Nature 343:177–180 (1990); Sucov et al., Proc. Natl. Acad. Sci. USA 87:5392–5396(1990); Nicholson et al., EMBO J. 9:4443–4454 (1990); Zelent et al., EMBO J. 10:71–81 (1991)). With extracts of COS-1 cells transfected with mRAR-γ1, a specific complex was obtained (arrow 1 in FIG. 1C, lane 2) which disappeared when the oligonucleotide was mutated (RARE-βm, see Materials and Methods) (FIG. 1C, lane 1).

The above complex was shifted to a more slowly migrating species (arrow 2 in FIG. 1C) following the addition of the monoclonal antibodies (Ab1γ1(A1) and Ab2γ(mF) (FIG. 1C, lanes 3 and 4). However, Ab5γ(D2) was less effective in inducing such a shift (FIG. 1C, lane 5.). Similarly, the addition of either Ab1γ1(A1) (see Nicholson et al., EMBO J. 9:4443–4454 (1990)) or Ab4γ(hF) (See Vasios et al., EMBO J. 10:1149–1158 (1991)) resulted in a shift of the probe-receptor complex obtained with extracts of hRAR-γ1 transfected cells. As expected the probe-receptor complexes formed with mRAR-γ2-transfected cells were clearly shifted with Ab2γ(mF) and Ab5γ(D2), whereas no shift was observed with Ab1γ1(A1) (data not shown). In contrast, monoclonal antibodies specifically directed against either mRAR-α1 [Ab9α(hF)] or mRAR-β [Ab7β(A1)] did not induce any shift of the probe-RAR complex obtained with COS-1 cells expressing mRAR-γ1 (FIG. 1C, lanes 6 and 7). Furthermore none of the monoclonal antibodies raised against mRAR-γ1 led to a shift of the probe-RAR complex obtained with COS-1 cells expressing either mRAR-α1 or mRAR-β2 (FIG. 1C, lanes 10 and 16, and data not shown), thus confirming that they are specific for RAR-γ isoforms.

C) Detection of RAR-γ isoforms in F9 embryonal-carcinoma cells and mouse embryos It was investigated whether all of the RAR-γ antibodies characterized above could detect the presence of RAR-γ isoforms in mouse F9 embryonal carcinoma cells and mouse embryos. mRAR-γ1 and mRAR-γ2 messenger RNAs have indeed been found in F9 cells and in mouse embryos at various stages of development (Zelent et al., Nature 339:714–717 (1989); Kastner et al., Proc. Natl. Acad. Sci. USA 87:2700–2704 (1990)). The possible presence of mRAR-γ isoforms was first investigated by Western blotting using nuclear extracts from either F9 cells (treated or not with RA) or mouse embryos. No signal was detected when the monoclonal antibodies Ab1γ1(A1), Ab5γ(D2) and Ab2γ (mF) were used (FIG. 2A, lanes 7–15 and data not shown). However, with the RPγ(mF) antiserum a signal corresponding to a protein with an apparent molecular weight of 85 kDa was detected, instead of the expected 51 kDa cloned RAR-γ1 molecule (FIG. 2A, lanes 2 and 3, and 17–20 arrow). This signal, which was specific since it disappeared after antibody depletion of the antiserum (FIG. 2A, lanes 5 and 6 and 22), may correspond to a 85 kDa protein bearing a similar cross-reacting epitope(s). The lack of signals with the monoclonal antibodies suggested that the epitopes recognized by these antibodies could be modified post-translationally in F9 cells and mouse embryos, and/or that the RAR-γ proteins may be synthesized in amounts too low to be detectable by Western blotting.

To investigate this immunoprecipitation experiments using the same cell and embryo extracts were performed. A protein with the expected RAR-γ1 molecular weight (51 kDa, filled arrow) was revealed on Western blots using RPγ(mF) following immunoprecipitation of nuclear extracts of mouse embryos with either Ab1γ1(A1) (FIG. 2B, lane 3), Ab2γ(mF) (FIG. 2B, lane 4) or, Ab5γ(D2) (FIG. 2B, lane 5). Note that, to be seen, these signals required that approximately 1 mg of nuclear proteins was immunoprecipitated. However, they were specific since they disappeared when the NC filter was revealed with antibody-depleted RPγ(mF) (data not shown). Using F9 cell extracts, two signals corresponding either to a molecular mass similar to that of RAR-γ2 (~48 kDa) or to a lower one (~42 kDa), were specifically immunoprecipitated from 1 mg of nuclear protein with Ab2γ(mF) (FIG. 2C, lane 4) and Ab5γ(D2) (FIG. 2C, lane 5). However no signal was seen when F9 cell extracts were immunoprecipitated with Ab1γ1(A1).(FIG. 2C, lane 3). The same pattern was observed whether the F9 cells were treated or not for 24 hours with RA (data not shown). Moreover, the obtained signal was not increased when the three monoclonal antibodies were added together (data not shown).

D) Phosphorylation of mouse RAR-γ1

Figure 3:
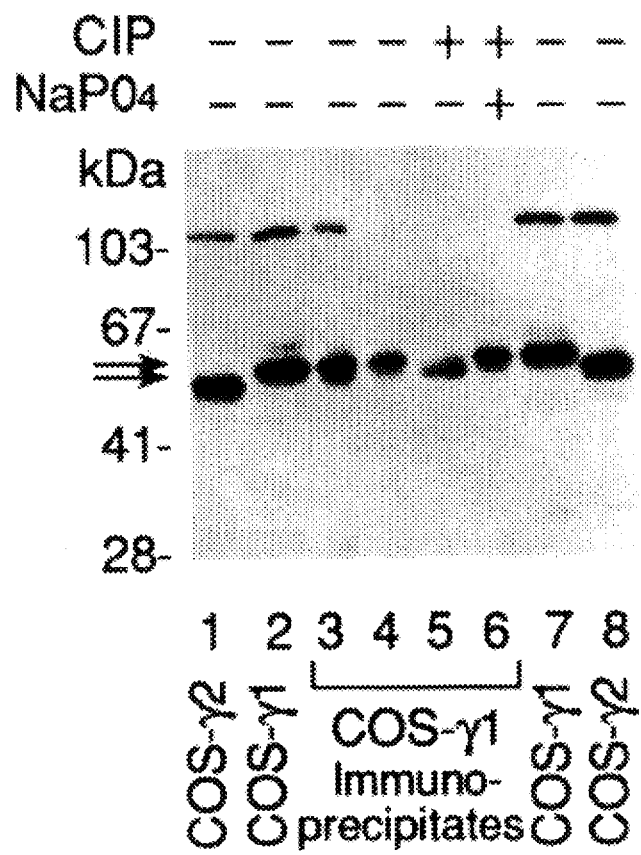

Multiple electrophoretic species were seen for the mRAR-γ1 protein made in COS-1 cells, and revealed with antibodies Ab1γ1(A1), Ab2γ(mF) and RPγ(mF) (FIG. 1A and 2A), which suggests the possible occurrence of post-translational modifications. Protein phosphorylation often alters mobility during SDS-PAGE. Thus Ab2γ(mF) immunoprecipitates of mRAR-γ1 synthesized in transfected COS-1 cells were treated with calf intestinal alkaline phosphatase (CIP) in the presence or absence of sodium phosphate, a phosphatase inhibitor. In the absence of inhibitor, CIP treatment increased the mobility of mRAR-γ1, as compared to the untreated controls (FIG. 3, lanes 4 and 5). This effect was no longer visible following phosphatase treatment in the presence of inhibitor (FIG. 3, lane 6).

In order to confirm these results, we examined the phosphorylation state of RAR-γ1 and the effect of the retinoic acid treatment on phosphorylation. mRAR-γ1-transfected COS-1 cells were labelled with [$^{32}$P] orthophosphate in the presence or absence of RA ($10^{-7}$M) and the RAR-γ1 proteins were immunoprecipitated with the specific monoclonal antibodies Ab2γ(mF). A phosphorylated protein with an apparent molecular mass of 51 kDa and corresponding to RAR-γ1 (as determined by immunoblotting on the same NC filters, using RPγ(mF) and alkaline phosphatase conjugated goat anti-rabbit antibody) was detected (FIG. 4A, lanes 2, 3, 6 and 7). No variation in the phosphorylation intensity was seen after 4 hours of RA treatment (FIG. 4A, compare lanes 6 and 7). No phosphorylated protein was detectable in COS-1 cells which had been transfected with the parental expression vector pSG5 (FIG. 4A, lanes 4, 5, 8 and 9). These results indicate that the RAR-γ1 protein exist in a phosphorylated state.

In order to investigate where RAR-γ1 was phosphorylated, we constructed three expression vectors encoding chimeric proteins, Gal4-RAR-γ1 (A/B), Gal4-RAR-γ1 (EF) and Gal4-RAR-γ1 (DEF) in which the Gal4 (1–14.7) DNA binding domain is fused with either the A/B, EF or DEF regions of mRAR-γ1, respectively. These chimeric proteins also contained the F region of the estrogen receptor (ER) against which immunoprecipitating monoclonal antibodies (ABF3) have been raised (Richotte-Egly et al., Genes Develop. 4:137–150 (1990)).

COS-1 cells were transfected, labelled with [$^{32}$P] and the chimeric proteins were immunoprecipitated with the monoclonal antibody AbF3. The expected chimeric proteins were revealed after electrophoresis by immunoblotting (FIG. 4B, lanes 1, 3, 5 and 7, arrows; Gal4-Exon(8) is a chimeric protein which contains the Gal4 DNA binding domain fused to the ER region F; see Webster et al., EMBO J. 8:1441–1446 (1989)). Autoradiography of the same NC filters revealed that the proteins encoded by the Gal4-RAR- γ1(A/B) and Gal4-RAR-γ1(DEF) expression vectors, were phosphorylated (FIG. 4B, lanes 4 and 8). The phosphorylation of GAL4-RAR-γ1 (DEF) was not affected by RA treatment (data not shown). However, the protein encoded by the Gal4-RAR-γ1(EF) expression vector was not labelled either in the presence or absence of RA (FIG. 4B, lane 6), indicating that the D region, but not the EF region, contains phosphorylation site(s). No [$^{32}$P] labelling was associated with the Gal4-Exon(8) protein indicating that the Gal4-DNA binding domain as well as the F region of the estrogen receptor were not phosphorylated (FIG. 4B, lane 2).

DISCUSSION

In the present study, we have described the production, characterization and utilization of antipeptide antibodies that are directed against RAR-γ isoforms. Four monoclonal antibodies directed against the A1 region [Ab1γ1(A1)], the D2 region [Ab5γ(D2)] and the F region [Ab2γ(mF) and Ab4γ(hF)] and one rabbit polyclonal antiserum directed against the mouse F region [RPγ(mF)], were obtained and were specific for the predominant RAR-γ1 isoform. All these antibodies immunoprecipitate and recognize specifically by immunoblotting a 51 kDa protein in nuclear extracts of RAR-γ1 transletted COS-1 cells. This apparent molecular mass is as predicted from the RAR-γ1 cDNA sequence (Krust et al., Proc. Natl. Acad. Sci. USA 86:5310–5314 (1989)). This 51 kDa protein has a nuclear localization and is absent from cytosolic extracts as confirmed by immunostaining of RAR-γ1 transfected cells (data not shown). Additionally, in DNA binding assays, the antibodies specifically retard the migration of the complex obtained between extracts of transfected COS-1 cells and the RA responsive element of the RAR-β2 promoter (RARE-β2). These results indicate that our antipeptide antibodies specifically recognize the corresponding epitope of RAR-γ1 protein produced in cells transletted with expression vectors containing the RAR-γ1 cDNAs. The antibodies directed against the D2 [Ab5γ(D2)] and F[Ab2γ(mF), Ab4γ(hF)and RPγ(mF)] regions recognized also the RAR-γ2 isoform, whereas Ab1γ1(A1) did not, in agreement with the presence of a different A region (A2) in the RAR-γ2 isoform.

The three monoclonal antibodies Ab1γ1(A1), Ab2γ(mF) and Ab5γ(D2) recognized either human or mouse RAR-γ proteins. However, the polyclonal rabbit antibodies RPγ (mF) even though it was raised against the same peptide SP14 (mouse F region) which yielded the monoclonal Ab2γ(mF), recognized specifically the mouse RAR-γ isoforms and not their human counterparts. Conversely, Ab4γ (hF) was specific for human RAR-γ proteins, although the sequence of the peptide SP25 used as antigen (human F region) contains amino acid residues overlapping the sequence of the mouse counterpart (SP14).

These antibodies allowed the detection of endogenous RAR-γ isoforms in mouse embryos and F9 embryonal carcinoma cells nuclear extracts. In both cases mRAR-γ proteins were not detectable by immunoblotting, but could be immunoprecipitated from large amounts (1 mg protein) of nuclear extracts. Thus, the endogenous mRAR-γ isoforms appear to be present in low amounts in mouse embryos and F9 cells. A species corresponding to the mRAR-γ1 isoform (51 kDa) was specifically immunoprecipitated from mouse embryos nuclear extracts with monoclonal antibodies directed against either the A1, D2 of F regions. In F9 cells nuclear extracts, one RAR-γ species with a molecular weight corresponding to that of the RAR-γ2 isoform (48 kDa) was immunoprecipitated as well as a second species with a lower molecular weight (42 kDa). As previously reported for mRAR-γ transcripts (Kastner et al., Proc. Natl. Acad. Sci. USA 87:2700–2704 (1990)) the intensity of these signals was not affected by RA treatment of F9 cells. Since these species were specifically immunoprecipitated with Ab2γ (mF) and Ab5γ(D2), but not with Ab1γ1(A1), they may correspond to the isoform mRAR-γ2 and to a proteolytic product of this isoform. Alternatively, the lower species may correspond to the isoforms mRAR-γ5 and/or mRAR-γ6, even though these mRNAs appear to be present in very low amounts in F9 cells (Kastner et al., Proc. Natl. Acad. Sci. USA 7:2700–2704 (1990)). Further studies with specific antibodies directed against the mRAR-γ2 isoform are required to investigate these possibilities.

The present antibodies allowed us to demonstrate that RAR-γ1 is modified post translationally. mRAR-γ1 appears to be a phosphoprotein as are steroid hormone receptors (for review see Auricchio, F., J. Steroid Biochem. 32:613–622 (1989)). In vitro phosphatase treatment converted mRAR-γ1 to a faster electrophoretic form as previously described for the glucocorticoid and progesterone receptors (Hoeck et al., J. Biol. Chem. 264:14396–14402 (1989); Denner et al., J. Biol. Chem. 265:16548–16555 (1990a)), or for other transcription factors such as Gal4 (Mylin et al., Genes Develop. 3:1157–1165 (1989)), the heat shock transcription factor (Sorger et al., Cell 54:855–864 (1988)), the adenovirus E1A protein (Dumont et al., J. Virol. 63:987–991 (1989); Smith et al., J. Virol. 63:1569–1577 (1989)), the octamer transcription factor (Tanaka et al., Cell 60:375–386 (1990)), the cAMP-responsive transcription factor CREB (Gonzalez et al., Mol. Cell. Biol. 11:1306–1312 (1991)) and Fos (Ofir et al., Nature 348:80–82 (1990)). Furthermore mRAR-γ1 could be labelled in vivo with [$^{32}$P], both in the absence and presence of RA. With the help of a chimeric construction in which the Ga14(1–147) DNA binding domain was fused with the A/B, EF or DEF regions of mRAR-γ1, we found that the A/B and D regions of RAR-γ1 contain phosphorylation sites. Whether the DNA binding domain (region C) may also be phosphorylated remains to be investigated.

Although the precise location of the phosphorylated residues of RAR-γ1 is unknown, we note that both the A/B and D regions correspond to the portion of the protein that contains most of serine residues belonging to consensus phosphorylation motifs for protein kinases such as cyclic AMP dependent kinase (RXSX), proline dependent kinase (XSPX), casein kinases I (EXXS) and II (SXXS, SXXE, SXXP), and glycogen synthase kinase 3 (XSXXXSX) (see Kemp et al., T.I.B.S. 15:342–346 (1990) and FIG. 6). Phosphorylation in the A/B domain has been also reported for the glucocorticoid (Hoeck et al., J. Biol. Chem. 265:5403–5408 (1990)) and thyroid hormone (Goldberg et al., EMBO J. 7:2425–2433 (1988); Glineur et al., Oncogene 4:1247–1254 (1989)) receptors. Moreover phosphorylation of serine residues has been observed in both the N-terminal region and the central D region (between the DNA and hormone binding domains) of the progesterone receptor (Denner et al., J. Biol. Chem. 265:16548–16555 (1990a)). However, phosphorylation of RAR-γ1 occurs irrespective of the presence of RA, in contrast to what has been found for the progesterone receptor whose phosphorylation increases in the presence of hormone (Denner et al., Science 250:1740–1743 (1990b)).

The possible effect of phosphorylation on the function of RAR-γ is unknown. In this respect, we note that the role of phosphorylation on the function of other members of the nuclear receptor superfamily (see above for references) remains also to be discovered. Phosphorylation could affect the tertiary structure of RAR-γ, which may result in the "unmasking" of a transcriptional activation function, as it was recently proposed in the case of the transcription factor CREB (Gonzalez et al., Mol. Cell. Biol. 11:1306–1312 (1991)). Phosphorylation may also control the rate of nuclear transport of RAR-γ as it was shown in the case of SV40 T antigen whose nuclear localization signal (NLS) is flanked by a casein kinase II site (Rihs et al., EMBO J. 10:633–639 (1991)). We note in this respect that the D region of RAR-γ contains casein kinase II sites as well as stretches of basic amino acids which may correspond to NLS. Site directed mutagenesis of the potential phosphorylation sites in RAR-γ is obviously required to investigate this and other possibilities.

SUMMARY OF THE ANTIBODIES GENERATED USING THE ABOVE DESCRIBED PROCEDURES

The following table presents a list of antibodies, peptides used in generating the antibody, and the specificity of the antibody generated using the above-described procedures.

RABBIT POLYCLONAL ANTIBODIES AGAINST RAR-γ1 CLONED RECEPTOR

| Experimental name Rabbit | Usual name | Domain Region | Peptide | Mouse Western ICC | SDS | Human Western ICC | SDS | Number of bands by Western SDS | Gel shift assay h | m | Immuno Precipitation Mouse |
|---|---|---|---|---|---|---|---|---|---|---|---|
| rabbit 94 | RPγ(mF) | F | p14 (mouse) 436–451 | + | + | – | – | 2–3 | | | + |
| rabbit 96 | RPγ₁(A₁) | A | p15 (39–50) | + | + faible | + | ± | 1(+2?) | | | ND |
| rabbit 101 | RPγ (hF) | F | p25 | – | – | + | + | 1(+1) | | | ND |
| rabbit 116 | RPγ (hF) | | (human) 428–441) | – | – | + | + | 1(+1) | | | ND |
| rabbit 181 | RPγ (hF) | F | p25 | – | – | + | ±? | | | | ND |
| rabbit 182 | RPγ (hF) | | | | | | | | | | ND |

MONOCLONAL ANTIBODIES AGAINST RAR-γ1 CLONED RECEPTOR

| Experimental name | Usual name | Domain Region | Peptide | Classe | Mouse Western ICC | SDS | Human Western ICC | SDS | Number of bands by Western SDS | Gel shift assay h | m | Immuno Precipitation Mouse |
|---|---|---|---|---|---|---|---|---|---|---|---|---|
| 1γ-9D6.3.3 (hRARγ/Ab1.9D) | Ab1γ₁(A₁) | A₁ | p15 (39–50) | IgM | ± | ± | ± | ± | | | | ND |
| 1γ-9F4.14.4 (hRARγ/Ab1.9F) | Ab1γ₁(A₁) | A₁ | p15 | IgM instable | | | | | | | | ND |
| 1γ-8D7.2.4 (hRARγ/Ab1.8) | Ab1γ₁(A₁) | A₁ | p15 | Ascite IgG1 SFRi | + | + | + | + | 2 bands | + | + | + |
| 2γ-2C5.24.3 (hRARγ/Ab2) | Ab2γ (mF) | F | p14 (mouse) 436–451 | Ascite IgG1 SFRi | + | + | + | + | 2–3 | + | + | + |
| 3γ-7D3.2 | Ab3γ (hF) | F | p25 (human 428–441) | instable | | ± | ± | | | | | ND |
| 4γ-7A11.1 (hRARγ/Ab4) | Ab4γ (hF) | F | p25 | Ascite IgG SFRi | – | – | + | + | 2–3 | + | – | + |
| 5γ-6A10.2.4 (hRARγ/Ab5.6) | Ab5γ (D₂) | D2 | p81 172–183 | Ascite IgG1 SFRi | + | + | + | + | 1–2 | ± | ± | + |
| 5γ-10G11.4.2 (hRARγ/Ab5.10G) | Ab5γ (D) | D2 | p81 | IgG1 | + | + | + | + | 1–2 | ND | | ND |
| 5γ-10D3.4.1 (hRARγ/Ab5.10D) | Ab5γ (D₂) | D2 | p81 | IgG1 | + | + | + | + | 1–2 | ND | | ND |
| 22α-3E4.1 | | D1 | pB33 | | | | | | | | | – |

MONOCLONAL ANTIBODIES AGAINST RAR-γ2 CLONED RECEPTOR

| Experimental name | Usual name | Domain Region | Peptide | Classe | Mouse Western ICC | SDS | Human Western ICC | SDS | Number of bands by Western SDS | Gel shift assay h | m | Immuno Precipitation Mouse |
|---|---|---|---|---|---|---|---|---|---|---|---|---|
| 10γ-297.26.2 | Ab10γ2 (A₂) | | p82 | IgG₁ | + | – | ND | ND | | | | + |
| 10γ-4E3.9.5 | Ab10γ2 (A₂) | A2 | (22–34) | IgG₁ | + | – | ND | ND | | | | ± |
| 10γ-10F3.43.5 | Ab10γ2 (A₂) | | | IgG1 Ascite | + | – | ND | ND | | | | + |
| 10γ-4D3.2.12 | Ab10γ2 (A₂) | | | IgG₁ SFRI | + | – | ND | ND | | | | + |

Note that regions B to F are principle common to all γ isoforms.

The present invention is not to be limited in scope by the cell lines deposited and the examples given since the deposited embodiments are intended as examples illustrating one of the aspects of the invention and all antibodies and cell lines which are functionally equivalent are within the scope of the invention. Various modifications of the invention in addition to those shown in the art and from the foregoing description are anticipated by the present invention. Such modifications are intended to fall within the scope of the appended claims.

What is claimed is:

1. An isolated mouse monoclonal antibody which binds selectively to human RAR-γ, wherein said antibody binds to the SP25 peptide, and said antibody binds to both native and denatured forms of said RAR-γ.

2. An isolated mouse monoclonal antibody which binds selectively to both mouse and human RAR-γ1, but not RAR-γ2, wherein said antibody binds to the SP 15 peptide, and said antibody binds to both native and denatured forms of said RAR-γ1.

3. An isolated mouse monoclonal antibody which selectively binds to the region of both mouse and human RAR-γ, wherein said antibody binds to the SP14 peptide, and said antibody binds to both native and denatured forms of said RAR-γ.

4. An isolated mouse monoclonal antibody which selectively binds to the D2 region of both mouse and human RAR-γ, wherein said antibody binds to the SP81 peptide, and said antibody binds to both native and denatured forms of said RAR-γ.

5. An isolated mouse hybridoma which produces a monoclonal antibody which binds selectively to human RAR-γ, wherein said antibody binds to the SP25 peptide, and said antibody binds to both native and denatured forms of said RAR-γ.

6. An isolated mouse hybridoma which produces a monoclonal antibody which binds selectively to both human and mouse RAR-γ1, but not to RAR-γ2, wherein said antibody binds to the SP15 peptide, and said antibody binds to both native and denatured forms of said RAR-γ1.

7. An isolated mouse hybridoma which produces a monoclonal antibody which binds selectively to the F region of both human and mouse RAR-γ, wherein said antibody binds to the SP14 peptide, and said antibody binds to both native and denatured forms of said RAR-γ.

8. An isolated mouse hybridoma which produces a monoclonal antibody which binds selectively to the D2 region of both human and mouse RAR-γ, wherein said antibody binds to the SP81 peptide, and said antibody binds to both native and denatured forms of said RAR-γ.

9. The antibody of any one of claims 1, 2, 3 and 4 wherein said antibody is detectably labeled.

10. The antibody of any one of claims 1, 2, 3 and 4 wherein said antibody is immobilized on a solid support.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
  ( A ) LENGTH: 12 amino acids
  ( B ) TYPE: amino acid
  ( D ) TOPOLOGY: linear ( i i ) MOLECULE TYPE: peptide ( i x ) FEATURE:
  ( A ) NAME/KEY: CDS
  ( B ) LOCATION: 1..633

( x i ) SEQUENCE DESCRIPTION: SEQ ID NO:1:

Phe Glu His Leu Ser Pro Ser Phe Arg Gly Leu Gly
 1               5                   10

( 2 ) INFORMATION FOR SEQ ID NO:2:

( i ) SEQUENCE CHARACTERISTICS:
  ( A ) LENGTH: 14 amino acids
  ( B ) TYPE: amino acid
  ( D ) TOPOLOGY: linear ( i i ) MOLECULE TYPE: peptide ( i x ) FEATURE:
  ( A ) NAME/KEY: CDS
  ( B ) LOCATION: 1..1611

( x i ) SEQUENCE DESCRIPTION: SEQ ID NO:2:

Gln Pro Gly Pro His Pro Asn Ala Ser Ser Glu Asp Glu Val
 1               5                   10

( 2 ) INFORMATION FOR SEQ ID NO:3:

( i ) SEQUENCE CHARACTERISTICS:
  ( A ) LENGTH: 16 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:3:

Ser Ser Glu Asp Glu Ala Pro Gly Gly Gln Gly Lys Arg Gly Gln Ser
 1               5                   10                  15

( 2 ) INFORMATION FOR SEQ ID NO:4:

( i ) SEQUENCE CHARACTERISTICS:
  ( A ) LENGTH: 12 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:4:

Lys Glu Glu Gly Ser Pro Asp Ser Tyr Glu Leu Ser (2) INFORMATION FOR SEQ ID NO:5:

(i) SEQUENCE CHARACTERISTICS:
　　　　(A) LENGTH: 16 amino acids
　　　　(B) TYPE: amino acid
　　　　(D) TOPOLOGY: linear (ii) MOLECULE TYPE: peptide (ix) FEATURE:
　　　　(A) NAME/KEY: CDS
　　　　(B) LOCATION: 1..513

(xi) SEQUENCE DESCRIPTION: SEQ ID NO:5:

```
Ser Ser Glu Asp Glu Val Pro Gly Gly Gln Gly Lys Gly Gly Leu Lys
 1               5                  10                  15
```

(2) INFORMATION FOR SEQ ID NO:6:

(i) SEQUENCE CHARACTERISTICS:
　　　　(A) LENGTH: 14 amino acids
　　　　(B) TYPE: amino acid
　　　　(D) TOPOLOGY: linear (ii) MOLECULE TYPE: peptide (xi) SEQUENCE DESCRIPTION: SEQ ID NO:6:

```
Lys Pro Gly Pro His Pro Lys Ala Ser Ser Glu Asp Glu Ala
 1               5                  10
```